(12) United States Patent
Hellstrom et al.

(10) Patent No.: US 8,076,085 B2
(45) Date of Patent: Dec. 13, 2011

(54) METHODS AND MEANS RELATING TO HEPATITIS B INFECTION

(75) Inventors: Ulla Hellstrom, Stockholm (SE); Staffan Sylvan, Uppsala (SE)

(73) Assignee: HBV Theranostica AB, Stockholm (SE)

( * ) Notice: Subject to any disclaimer, the term of this patent is extended or adjusted under 35 U.S.C. 154(b) by 0 days.

(21) Appl. No.: 10/578,848

(22) PCT Filed: Oct. 22, 2004

(86) PCT No.: PCT/EP2004/011958
§ 371 (c)(1), (2), (4) Date: Jul. 24, 2006

(87) PCT Pub. No.: WO2005/050214
PCT Pub. Date: Jun. 2, 2005

(65) Prior Publication Data
US 2007/0054264 A1 Mar. 8, 2007

Related U.S. Application Data

(60) Provisional application No. 60/519,152, filed on Nov. 12, 2003.

(30) Foreign Application Priority Data

Nov. 12, 2003 (GB) .................................. 0326416.5

(51) Int. Cl.
*G01N 33/53* (2006.01)
*C12Q 1/70* (2006.01)
*A61K 39/40* (2006.01)
(52) U.S. Cl. ........................... 435/7.1; 435/5; 424/161.1
(58) Field of Classification Search .................. None
See application file for complete search history.

(56) References Cited

U.S. PATENT DOCUMENTS

| 4,847,080 A * | 7/1989 | Neurath et al. ............... 530/324 |
| 5,204,096 A | 4/1993 | Neurath et al. | |

FOREIGN PATENT DOCUMENTS

| EP | 154902 A * | 9/1985 |
| EP | 0 250 253 | 12/1987 |
| EP | 448126 A * | 9/1991 |
| EP | 0 491 077 | 6/1992 |
| WO | 94/04922 | 3/1994 |

OTHER PUBLICATIONS

Paul, Fundamental Immunology, 5th Edition, 2003, pp. 718-720.*
Wei et al. Detection of anti-preS1 antibodies for recovery of hepatitis B patients by immunoassay, World J. Gastroenterol., 2002, 8(2):276-281.*
Zavaglia et al., Treatment of chronic hepatitis B (HBeAg-HBV DNA-positive) with lymphoblastoid alpha interferon with or without corticosteroids: short- and long-term follow-up, Italian Journal of Gastroenterology, Jul.-Aug. 1996 , 28 (6):324-331. Abstract.*
Wei et al., Detection of anti-preS1 antibodies for recovery of hepatitis B patients by immunoassay, World J Gastroenterol, 2002, 8(2):276-281.*
International Search Report for PCT/EP04/11958 dated Sep. 6, 2005.
Alberti et al., *Fine specificity of human antibody response to the PreS1 domain of hepatitis B virus*, Hepatology, vol. 12, No. 2, Aug. 1990, pp. 199-203, XP009052827.
Petit et al., *PreS1 antigen/antibody patterns following interferon therapy in acute and chronic hepatitis B*, J. Hepatol., vol. 20, No. 1, Jan. 1994, pp. 47-56, XP009052825.
Lai et al, "Viral hepatitis B", The Lancet 362:2089-2094 (2003).
Heathcote, E. Jenny, "Demography and Presentation of Chronic Hepatitis B Virus Infection", The American Journal of Medicine 121:S3-S11 (2008).
De Franchis et al, "EASL International Consensus Conference on Hepatitis B", Journal of Hepatology 39:S3-S25 (2003).
Chu, Chia-Ming, "Natural history of chronic hepatitis B virus infection in adults with emphasis on the occurrence of cirrhosis and hepatocellular carcinoma", Journal of Gastroenterology and Hepatology 15(Suppl S2):E25-E30 (2000).
Fattovich et al, "Long-Term Outcome of Hepatitis B e Antigen-Positive Patients with Compensated Cirrhosis Treated With Interferon Alfa", Hepatology 26:1338-1342 (1997).
Ikeda et al, "Interferon Decreases Hepatocellular Carcinogenesis in Patients with Cirrhosis Caused by the Hepatitis B Virus", Cancer 82(5):827-835 (1998).
Liaw and Chu, "Hepatitis B virus infection", The Lanced 373:S82-S92 (2009).
Liaw, Yun-Fan, "Hepatitis B virus replication and liver disease progression: the impact of antiviral therapy", Antivirus Therapy 11:669-679 (2006).
Cooksley, Graham, "The treatment of hepatitis B e antigen-positive chronic hepatitis B with pegylated interferon", Journal of Hepatology 39:S143-S145 (2003).
Craxi et al, "Interferon-α for HBeAg-positive chronic hepatitis B", Journal of Hepatology 39:S99-S105 (2003).
Wong et al, "Effect of Alpha-Interferon Treatment in Patients with Hepatitis B e Antigen-Positive Chronic Hepatitis B", Ann. Intern. Med. 119:312-323 (1993).

* cited by examiner

*Primary Examiner* — Zachariah Lucas
*Assistant Examiner* — Nicole Kinsey White
(74) *Attorney, Agent, or Firm* — Nixon & Vanderhye P.C.

(57) ABSTRACT

The present inventors have discovered that the presence of antibodies reactive with residues 94-117 of the PreS1 component of the hepatitis B surface antigen (HBsAg) in an individual with HBV infection correlates closely with the effectiveness of interferon (IFN) in treating the individual. Methods and means based on this finding are provided herein.

10 Claims, 22 Drawing Sheets

SEQUENCE LISTING

<160> NUMBER OF SEQ ID NOS: 4

<210> SEQ ID NO 1
<211> LENGTH: 24
<212> TYPE: PRT
<213> ORGANISM: Hepatitis B virus
<220> FEATURE:
<221> NAME/KEY: MISC_FEATURE
<222> LOCATION: (2)..(2)
<223> OTHER INFORMATION: Xaa may be any amino acid. Preferably, Xaa is
      independently Ala or Val
<220> FEATURE:
<221> NAME/KEY: MISC_FEATURE
<222> LOCATION: (15)..(15)
<223> OTHER INFORMATION: Xaa may be any amino acid. Preferably, Xaa is
      independently Leu or Ile
<220> FEATURE:
<221> NAME/KEY: MISC_FEATURE
<222> LOCATION: (21)..(21)
<223> OTHER INFORMATION: Xaa may be any amino acid. Preferably, Xaa is
      independently Asp, Asn or Thr
<220> FEATURE:
<221> NAME/KEY: MISC_FEATURE
<222> LOCATION: (22)..(22)
<223> OTHER INFORMATION: Xaa may be any amino acid. Preferably, Xaa is
      independently Thr or Ser

<400> SEQUENCE: 1

Pro Xaa Ser Thr Asn Arg Gln Ser Gly Arg Gln Pro Thr Pro Xaa Ser
1               5                   10                  15

Pro Pro Leu Arg Xaa Xaa His Pro
            20

<210> SEQ ID NO 2
<211> LENGTH: 24
<212> TYPE: PRT
<213> ORGANISM: Hepatitis B virus

<400> SEQUENCE: 2

Pro Ala Ser Thr Asn Arg Gln Ser Gly Arg Gln Pro Thr Pro Leu Ser
1               5                   10                  15

Pro Pro Leu Arg Asn Thr His Pro
            20

<210> SEQ ID NO 3
<211> LENGTH: 24
<212> TYPE: PRT
<213> ORGANISM: Hepatitis B virus

<400> SEQUENCE: 3

Pro Ala Ser Thr Asn Arg Gln Ser Gly Arg Gln Pro Thr Pro Leu Ser
1               5                   10                  15

Pro Pro Leu Arg Thr Thr His Pro
            20

<210> SEQ ID NO 4
<211> LENGTH: 24
<212> TYPE: PRT
<213> ORGANISM: Hepatitis B virus

<400> SEQUENCE: 4

Pro Ala Ser Thr Asn Arg Gln Ser Gly Arg Gln Pro Thr Pro Ile Ser
1               5                   10                  15

Pro Pro Leu Arg Asp Ser His Pro
            20

METHODS AND MEANS RELATING TO HEPATITIS B INFECTION

This application is the US national phase of international application PCT/EP2004/011958 filed 22 Oct. 2004 which designated the U.S. and claims benefit of GB 0326416.5, filed 12 Nov. 2003, and U.S. Provisional Application No. 60/519,152, filed 12 Nov. 2003, the entire contents of each of which are hereby incorporated by reference.

This invention relates to the use of interferon (IFN) to treat hepatitis B (HBV) infection and, in particular, to the identification of HBV patients for whom IFN treatment is likely to be beneficial.

Hepatitis B infection is associated with high morbidity and mortality (Niederau C. et al (1996) *The New England Journal of Medicine* 334, 1422-1427). HBV infection is associated with cirrhosis, liver failure, hepatocellular carcinoma and death (Dudley F J et al (1972) *Lancet* ii: 1388-1393; Hoofnagle J H et al (1983) Chronic type B hepatitis: Clinical course. In: *Viral Hepatitis and Delta Infection*. New York; Alan R Liss Inc, 1983; 41-53; Weissberg J et al (1984) *Annal Internal Medicine* 101: 613-616.; Fattovich G., et al (1986) *Hepatology* 6: 167-172; Popper H et al (1987) Hepatology 7: 764-772).

Several randomized clinical trials have reported that therapy with recombinant interferon alpha (IFN-alpha) offers significant clinical benefits. The rate of elimination of hepatits B e antigen (HBeAg) increased with IFN treatment from a low rate of spontaneous clearance of 5-10 percent to approximately 24-30 percent (Hoofnagle J H et al (1988) *Gastroenterology* 95: 1318-1325.; Alexander G J M et al (1987) *Lancet* 2: 66-69; Brook M G et al (1989) *Gut:* 130: 1116-1122; Saracco G et al (1989) *Hepatology* 10: 336-341.; Perillo R P et al (1990) *New England Journal of Medicine* 323: 295-301.; Tine F et al (1993) *Journal of Hepatology* 18: 154-162; Cooksley W G E et al (2003) *Journal of Viral Hepatitis* 10: 298-305). The interferon-induced elimination of hepatitis e antigen is accompanied of a reduced incidence of hepatocellular carcinoma (Yang H-I et al (2002) *The New England Journal of Medicine* 347: 168-174).

Given the side-effects associated with IFN treatment, the ability to identify those patients who are likely to respond to interferon therapy would be useful in making recommendations for treatment (Lau D T-Y et al (1998) *Journal of Viral Hepatitis* 5: 105-114).

A range of markers have been proposed for use in predicting whether a patient will respond to interferon treatment, including serum levels of transaminases, HBV-DNA, HBeAg, HBV preS1 antigen and IgM antibodies to HBcAg or HBeAg. (Krogsgaard et al, 1994 *Journal of hepatology* 21: 646-655; Brook et al, 1989b *Hepatology* 10: 761-763; Perillo et al, 1988 supra; Dienstag et al, 1995, *New Journal England Medicine* 333: 1657-1661; Villeneuve et al, 1996 *Cancer Journal Gastroenterology* 10: 21-25; Janssen et al, 1999 *Hepatology* 30: 238-243; Brunetto et al, 1993 *Journal of Hepatology* 19: 431-436; Marinos et al, 1994 *Hepatology* 19: 303-311).

PreS1 antigen (PreS1 Ag) is detectable in serum during HBV-infection and has been suggested to be a reliable marker for monitoring residual HBV replication in chronically infected patients receiving antiviral therapy as well a predictor of IFN response (Petit M A et al (1990) *Hepatology* 11: 809-814; Petit M A et al (1992a) *Archieves of Virology Suppl* 4: 105-112; Petit M A et al (1992b) *Virology* 187: 211-222; Petit M A et al (1994) *Journal of Hepatology* 20: 47-56; Feng et al, 1995 *Zhonghua Yixue Jianyan Zazhi* 18: 154-157; Ibarra et al, 1989 *Liver* 9: 153-158; Mi et al, 1999 *Chinese Medical Journal* 112: 321-324; Buffello-Le Guillou et al, 2000 *Journal of Viral Hepatitis* 7: 387-392).

A synthetic peptide analogue (preS1# 21-47) of a portion of the preS1 antigen is recognized by both cell receptors and anti-HBV antibodies. Furthermore, this peptide elicits antibodies reacting with native HBV. Among the preS1-specific peptides 1-21, 12-32, 32-53 and 94-117, only the peptide 12-32 is recognized strongly by human anti-HBV (Neurath et al, 1986 *Cell* 46: 429-436; Neurath A R (1988a) *Advances Virus Research* 34: 65-142; Neurath A R (1988b) *Ann.Inst.Pasteyr/Virol* 139: 13-38).

Serum antibodies with specificity for preS1 antigen have been demonstrated early in acute HBV-infection (Alberti et al, 1978 *British Medical Journal* 14: 1056-1058; Theilmann et al, 1986 *Hepatology* 6: 186-190; Hellström and Sylvan, 1988 *Progress in Medical Virology* 35: 76-106; Budowska et al (1990) *Hepatology* 12: 1271-1277; Budowska et al (1992) *Hepatology* 15: 26-32). 22.7% (15/66) patients with chronic hepatitis B were positive for antibody to the C-terminus (94-117) preS1 sequence that, unlike the acute-phase anti-(21-32) and anti-(32-47) reactivities, did not behave as a virus-precipitating antibody. More than half of 19 acute hepatitis B patients produced anti-preS1 (21-119) antibodies, during recovery of the disease, however, the response was found only in a few chronic patients (Wei et al (2002) *World Journal of Gastroenterology* 8: 276-281).

The present inventors have discovered that the presence of antibodies reactive with a specific portion of the PreS1 component of the hepatitis B surface antigen (HBsAg) antigen in a sample from an individual with HBV infection correlates closely with the effectiveness of interferon (IFN) in treating the individual.

One aspect of the invention provides a method of predicting whether an individual infected with hepatitis B virus (HBV) will respond to interferon (IFN) treatment, the method comprising;
  determining the presence or amount of antibodies reactive with a preS1 (94-117) peptide in a sample obtained from the individual.

The presence of antibodies reactive with a preS1 (94-117) peptide in the sample is indicative that the individual is a responder for whom the treatment will be beneficial (i.e. someone who will respond to IFN treatment).

An individual who is responsive to IFN treatment (i.e. a responder) may, in response to IFN treatment, show an improvement in one or more symptoms of HBV infection. For example, the level of one or more biomarkers associated with HBV infection, such as serum HBeAg levels, may be reduced or eliminated by IFN treatment of an individual who is responsive to the treatment.

A method as described herein may be used to determine whether or not an individual having hepatitis B virus (HBV) infection is a responder to interferon (IFN) treatment. A method may thus comprises identifying an individual having antibodies reactive with said peptide as a responder to IFN treatment.

An individual suitable for analysis using the present methods may have a chronic or an acute hepatitis B infection. The individual may show one or more symptoms of HBV infection, for example, the individual may be HBeAg positive.

An antibody reactive with a preS1 (94-117) peptide is an antibody molecule which binds or reacts with a preS1 (94-117) peptide.

In some embodiments, an antibody reactive with an antigen such as a preS1 (94-117) peptide may not show any significant binding to molecules other than the antigen (i.e. it may show specific binding). In some cases, an antibody may specifically bind to a particular epitope, such as the preS1 (94-117) epitope, which is carried by a number of antigens, in which case the antibody will be able to bind to the various antigens carrying the epitope. Thus, antibodies to the preS1 (94-117) epitope may also bind to other peptides and polypeptides comprising the preS1 (94-117) epitope, such as preS1 antigen.

An antibody molecule reactive with preS1 (94-117) whose presence is determined in accordance with the methods described herein, may be any immunoglobulin molecule which is produced by the immune system of the individual in response to a foreign antigen, for example IgG, IgD, IgM, IgA or, IgE. In preferred embodiments, an IgG molecule is detected.

A preS1 (94-117) peptide may consist of residues 94 to 117 of the HBV preS1 sequence. The HBV preS1 sequence may be from any subtype of HBV, including for example subtypes ayw, adyw, adw, $adw_2$ or adr. Peptide sequences of preS1 are described in Neurath A R, Kent S B (1988) *Advances Virus Research* 34: 65-142 and Neurath A R et al (1988) *Ann.Inst-.Pasteur/Virol* 139: 13-38.

$PX_1STNRQSGRQPTPX_2SPPLRX_3X_4HP$ (SEQ ID NO: 1)

where $X_1$, $X_2$, $X_3$ and $X_4$ may be any amino acid.
Preferably, $X_1$ is independently A or V.
Preferably, $X_2$ is independently L or I.
Preferably, $X_3$ is independently D, N or T.
Preferably, $X_4$ is independently T or S.

In some especially preferred embodiments, a preS1 (94-117) peptide may have one of the following sequences ($X_1$, $X_2$ and $X_3$ shown in bold);

(i)     PASTNRQSGRQPTPLSPPLRNTHP (SEQ ID NO: 2)

(ii)    PASTNRQSGRQPTPLSPPLRTTHP (SEQ ID NO: 3)

(iii)   PASTNRQSGRQPTPISPPLRDSHP (SEQ ID NO: 4)

Sequences of preS1 (94-117) from other HBV sub-types may be identified using conventional sequence analysis of public databases.

The presence of an antibody reactive with a preS1 (94-117) peptide may be determined by any convenient means and many suitable techniques are known in the art. For example, the sample may be contacted with a polypeptide comprising or consisting of a preS1 (94-117) epitope. Binding of antibody molecules in the sample to the preS1 (94-117) epitope of the polypeptide may then be determined, for example, by measuring immunocomplex formation between the preS1 (94-117) peptide and antibodies in the sample.

Binding of antibody molecules may be determined by any appropriate means. Tagging with individual reporter molecules is one possibility. The reporter molecules may directly or indirectly generate detectable, and preferably measurable, signals. The linkage of reporter molecules may be direct or indirect, covalent, e.g. via a peptide bond, or non-covalent. Linkage via a peptide bond may be as a result of recombinant expression of a gene fusion, encoding antibody and reporter molecule.

For example, an antibody or preS1 (94-117) peptide may be labelled with a fluorophore such as FITC or rhodamine, a radioisotope, or a non-isotopic-labelling reagent such as biotin or digoxigenin; antibodies containing biotin may be detected using "detection reagents" such as avidin conjugated to any desirable label such as a fluorochrome. Another possibility is to detect the binding of antibodies to the preS1 (94-117) antigen using a second antibody, for example in an ELISA assay system. The second antibody may, for example, be a non-human antibody that binds to human antibodies. Depending on the assay format employed, the second antibody may be immobilised or labelled with a detectable label.

In some embodiments, a labelled third antibody may be used to detect the binding of the second antibody.

The mode of determining binding is not a feature of the present invention and those skilled in the art are able to choose a suitable mode according to their preference and general knowledge.

Suitable approaches for determining the presence of antibodies as described above include Western Blotting, immunofluorescence, enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies. All of these approaches are well known in the art.

A preS1 (94-117) peptide as described above for use in methods of the invention may be generated wholly or partly by chemical synthesis or by recombinant expression from encoding nucleic acid.

PreS1(94-117) peptides may be readily prepared according to well-established, standard liquid or, preferably, solid-phase peptide synthesis methods, general descriptions of which are broadly available (see, for example, in J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, New York (1984); and Applied Biosystems 430A Users Manual, ABI Inc., Foster City, Calif.), or they may be prepared in solution, by the liquid phase method or by any combination of solid-phase, liquid phase and solution chemistry, e.g. by first completing the respective peptide portion and then, if desired and appropriate, after removal of any protecting groups being present, by introduction of the residue X by reaction of the respective carbonic or sulfonic acid or a reactive derivative thereof.

A peptide may be made resistant to proteolysis by the replacement of a —CONH— peptide bond by a ($CH_2NH$) reduced bond, a (NHCO) retro inverso bond, a ($CH_2$—O) methylene-oxy bond, a ($CH_2S$) thiomethylene bond, a ($CH_2CH_2$) carbon bond, a (CO—$CH_2$) cetomethylene bond, a ($CH_0H$—$CH_2$) hydroxyethylene bond), a (N—N) bound, a E-alcene bond or a CH=CH-bond.

Peptides may also be conveniently produced by expressing encoding nucleic acid in a recombinant expression system and isolating and/or purifying the expressed peptide. Suitable techniques for such expression are well known in the art.

A preS1 (94-117) peptide or polypeptide comprising a preS1 (94-117) epitope for use in a method described herein may be immobilised or non-immobilised i.e. free in solution.

A peptide may be immobilised, for example, by attachment to a solid support for use in an immunoassay. The support may be in particulate or solid form and may include a plate, a test tube, beads, a ball, a filter or a membrane. A peptide may, for example, be fixed to an insoluble support that is suitable for use in affinity chromatography. Methods for fixing peptides to insoluble supports are known to those skilled in the art. An immobilised peptide may be preferred, for example, in assay formats such as ELISA.

A solid support may be any material that is an insoluble matrix and can have a rigid or semi-rigid surface. Exemplary solid supports include, but are not limited to, substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like. Particular supports include plates, pellets, disks, capillaries, hollow fibers, needles, pins, solid fibers, cellulose beads, pore-glass beads, silica gels, polystyrene beads optionally cross-linked with divinylbenzene, grafted co-poly beads, polyacrylamide beads, latex beads, dimethylacrylamide beads optionally crosslinked with N-N'-bis-acryloylethylenediamine, and glass particles coated with a hydrophobic polymer.

If desired, the molecules to be added to the solid support can readily be functionalized to create styrene or acrylate moieties, thus enabling the incorporation of the molecules into polystyrene, polyacrylate or other polymers such as polyimide, polyacrylamide, polyethylene, polyvinyl, polydiacetylene, polyphenylene-vinylene, polypeptide, polysaccharide, polysulfone, polypyrrole, polyimidazole, polythiophene, polyether, epoxies, silica glass, silica gel, siloxane, polyphosphate, hydrogel, agarose, cellulose, and the like.

Another aspect of the invention provides an immunoassay solid support comprising a preS1 (94-117) peptide.

Preferred immunoassay solid supports are described above and include microtiter plates.

An immunoassay solid support may be produced by a method comprising:
(a) providing a solid support; and
(b) binding a preS1 (94-117) peptide to said support.

Techniques for binding peptides to a solid support are well-known in the art and are described in more detail above.

An immunoassay solid support may be useful in performing a method of the invention. A method of predicting whether an individual having hepatitis B virus (HBV) infection will respond to interferon (IFN) treatment, may comprise:
(a) providing an immunoassay solid support comprising a preS1 (94-117) peptide,
(b) combining a biological sample with said solid support under conditions which allow antibodies reactive with said peptide, when present in the biological sample, to bind to said peptide, and;
(c) detecting and/or measuring complexes formed between said antibodies and said peptide.

Complexes may be detected as described above by adding to the solid support from step (b), under complex forming conditions, a second antibody, wherein said second antibody binds to antibodies from said sample. For example, the second antibody may be an anti-IgG antibody. The second antibody may be detectably labelled.

For example, the methods described herein may be performed in an ELISA format. The wells of a microtiter plate may be coated with the peptide and a biological sample containing or suspected of containing antibody molecules is then added to the coated wells. After a period of incubation sufficient to allow antibody binding to the immobilized solid-phase peptide, the plate(s) can be washed to remove unbound moieties and a detectably labelled secondary binding molecule (e.g. labeled anti-IgG antibody) added. These molecules are allowed to react with any captured antibody bound to the peptide, the plate washed and the presence of the labeled antibodies detected using methods well known in the art.

Another aspect of the invention provides a kit for use in predicting whether an individual having hepatitis B will respond to interferon (IFN) treatment, the kit comprising a preS1 (94-117) peptide.

The peptide may be immobilised on a solid support, for example, a microtitre plate.

The kit may include instructions for use in a method for determining the presence of the antibodies of interest in a test sample. A kit may include one or more other reagents required for the method, such as secondary antibodies, detection reagents, buffer solutions etc. The secondary antibody may be labelled. A kit for use in determining the presence or absence of antibody of interest may include one or more articles and/or reagents for performance of the method, such as means for providing the test sample itself, e.g. a syringe for removing a sample and sample handling containers (such components generally being sterile).

Another aspect of the invention provides a method of treating an individual having hepatitis B comprising;
identifying the individual as responsive to interferon (IFN) treatment using a method as described herein, and;
administering IFN to said individual.

The IFN may be IFN-alpha, for example IFN-alpha 2a/2b or pegIFN-alpha 2a/2b, preferably IFN-alpha 2a or pegIFN-alpha 2a (Cooksley et al (2003) *J Viral Hepatitis* 10: 298-305, Manns et al (2001) *Lancet* 358:958-965).

IFN-alpha may be administered under the supervision of a medical practitioner in accordance with standard practice. For example, dosages of interferon-alpha of 2.5 to 5 million units (MU) per meter square (/MSq) of body surface area three times a week are commonly employed. Higher doses (up to 10 MU/MSq) of interferon may also be used and some studies indicate that higher doses have an improved response rate. Alternatively, 5 million units may be administered daily. IFN-alpha treatment is well known in the art and typically lasts four to six months.

The individual may also be treated with corticosteroids such as prednisolone.

Various further aspects and embodiments of the present invention will be apparent to those skilled in the art in view of the present disclosure. All documents referenced in this specification are incorporated herein by reference.

The skilled person will understand that the invention may be carried out with various combinations and sub-combinations of the features described above,-and all these combinations and sub-combinations, whether or not specifically described or exemplified, are encompassed by the invention.

Certain aspects and embodiments of the invention will now be illustrated by way of example and with reference to the figures and tables described below.

Figure 5A:
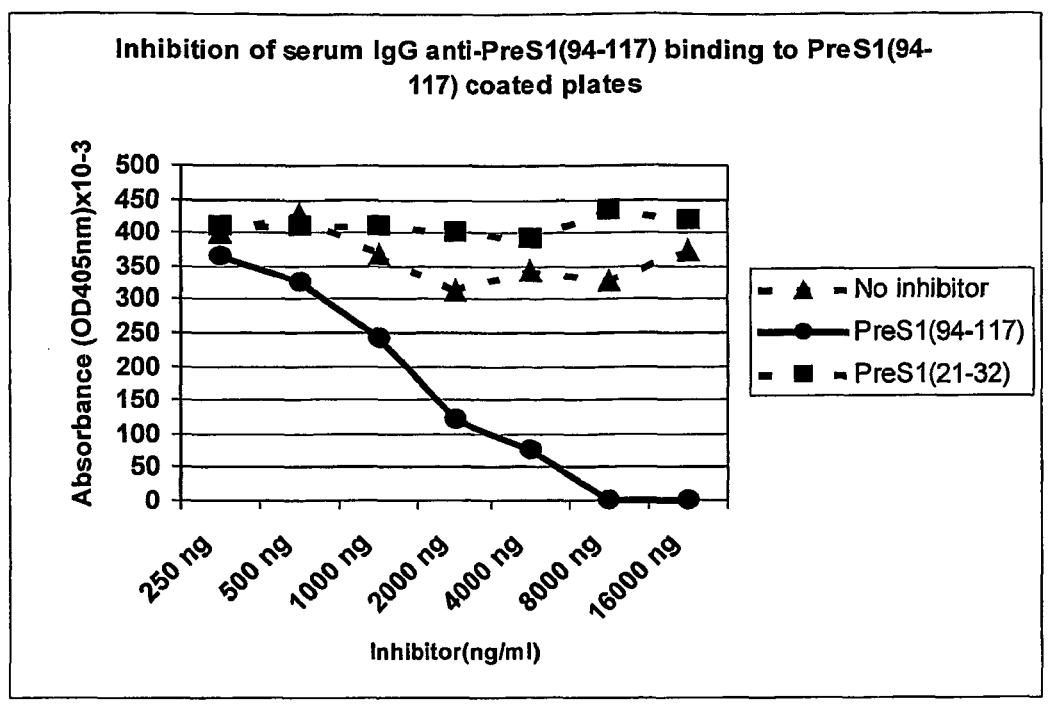
Figure 5B:
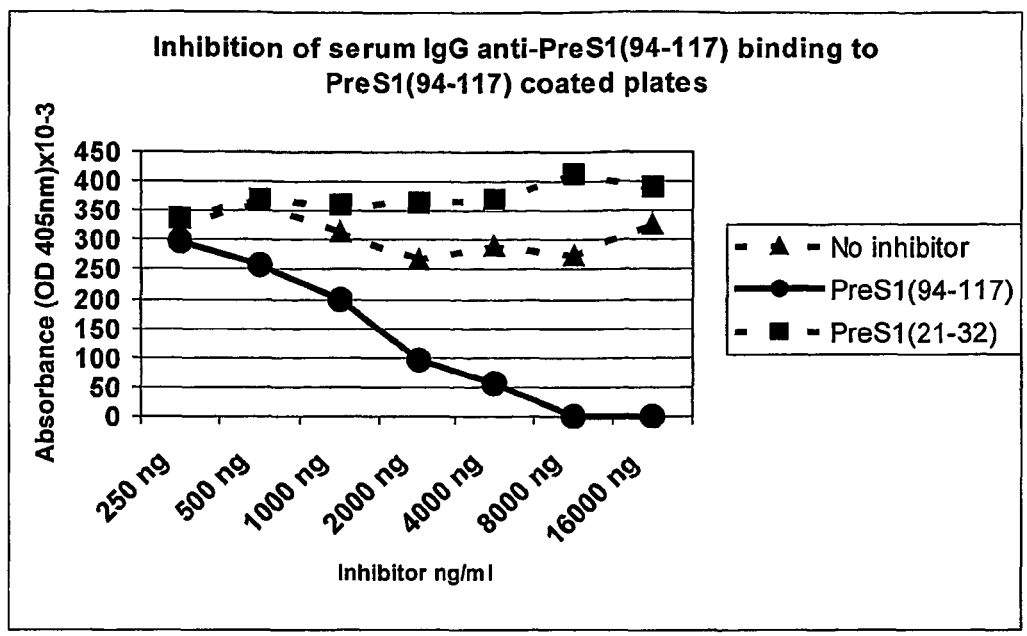
Figure 6A:
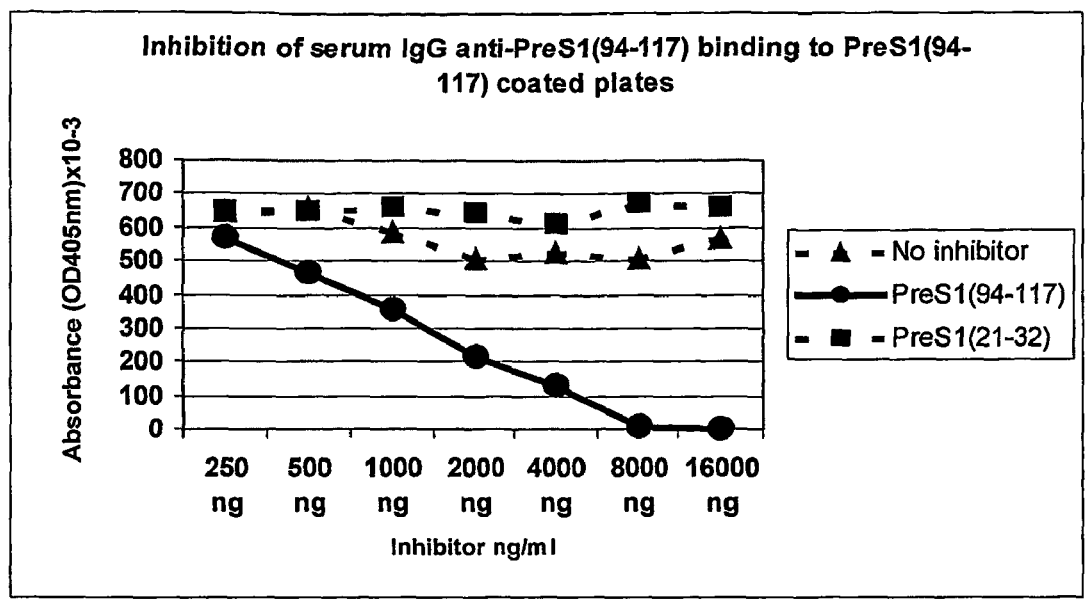
Figure 6B:
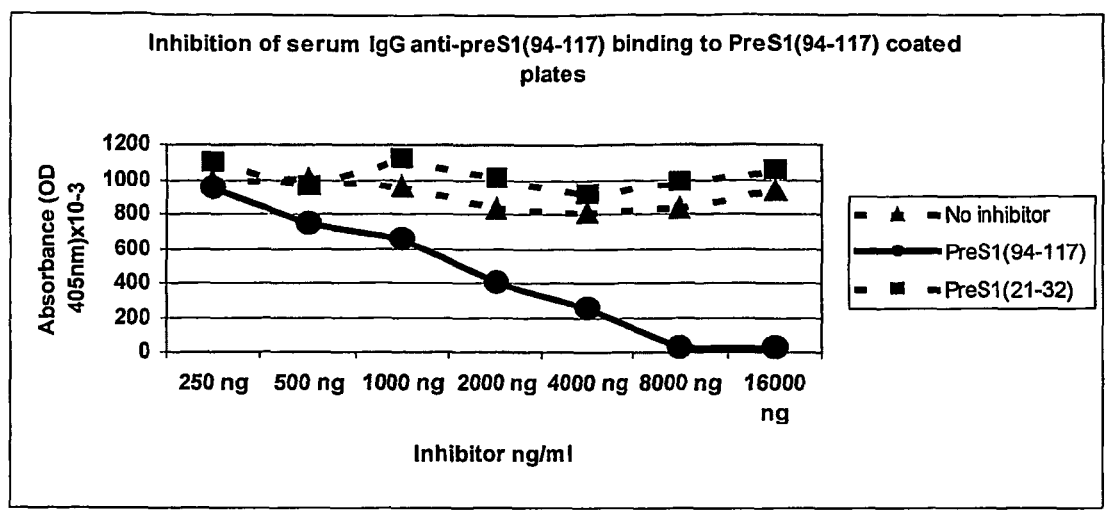

FIG. 5a shows the results of analysis of serum from one HBeAg+ patient with chronic HBV-infection, who later spontaneously seroconverted to anti-HBe reactivity. Serum was incubated with incubation buffer instead of inhibitor (s dotted line), preS1 (94-117, I dotted line) or preS1 (21-32, n dotted line) before addition to preS1 (94-117) coated ELISA plates. Data are given as OD values at 405 nm FIGS. 5b, 6a and 6b shows the results of analysis of serum of three HBeAg+ patients with acute resolving HB-infection. Samples were incubated with incubation buffer instead of inhibitor (s dotted line), preS1 (94-117, l dotted line) or preS1 (21-32, n dotted line) before addition to preS1 (94-117) coated ELISA plates. Data are given as OD values at 405 nm.

Figure 7:
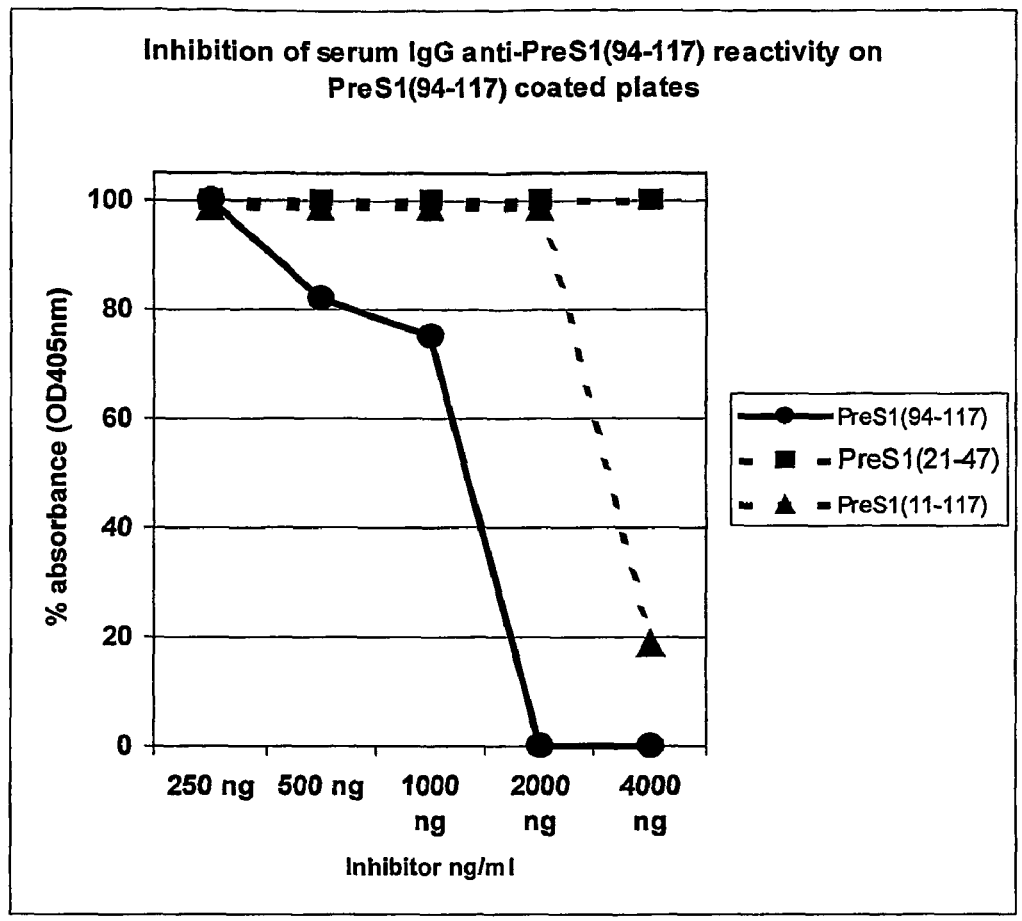

FIG. 7 shows the results of analysis of serum from a HBeAg+ chronic patient which was preincubated with preS1 (94-117, λ), the whole preS1 (11-117, σ) or the preS1 sequence(21-47) corresponding to the so called hepatocyte receptor (n).

Figure 8:
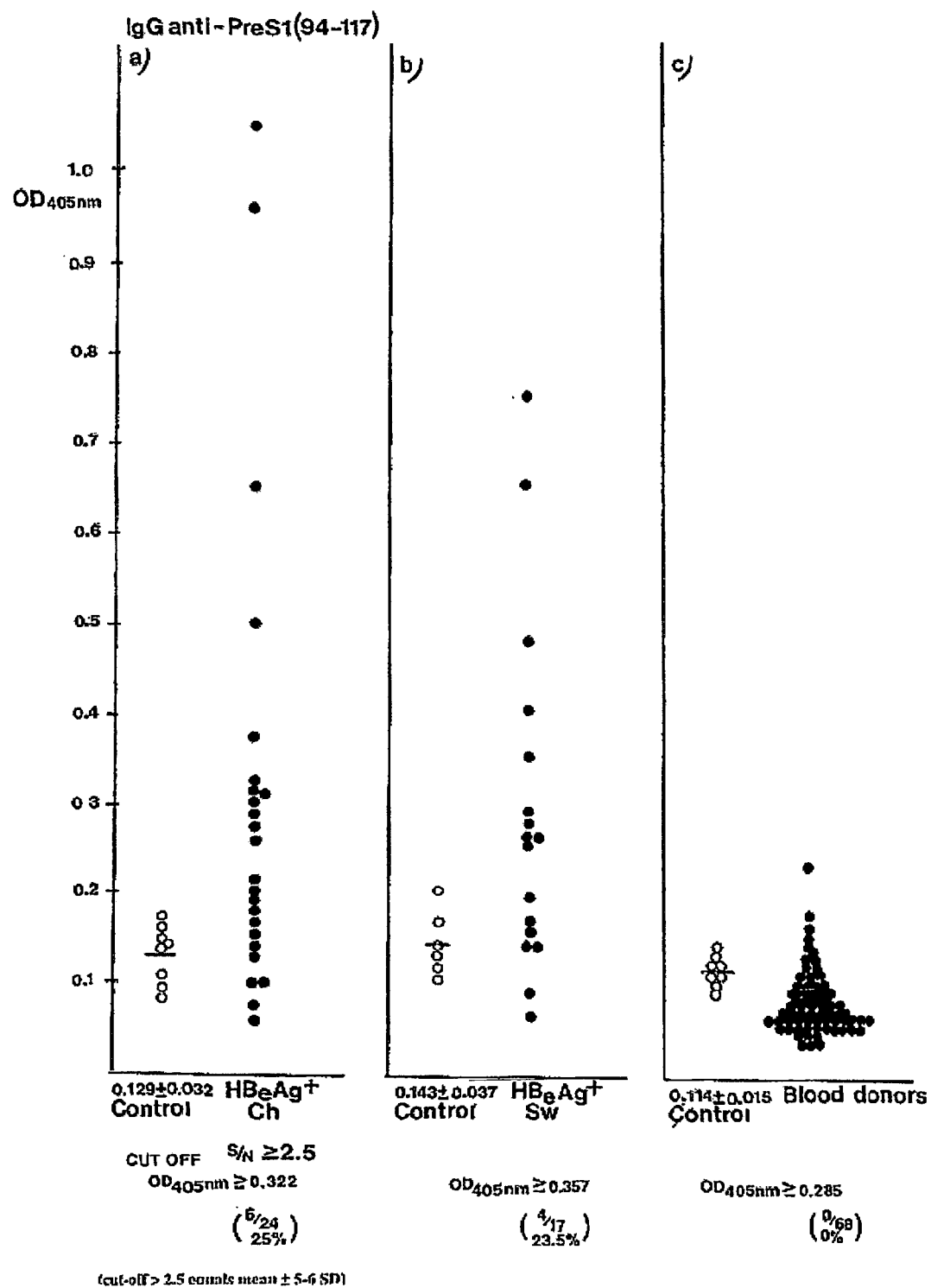

FIG. 8 shows the results of screening a cohort of 24 Chinese HBeAg+ patients (FIG. 8a), 17 Swedish HBeAg+ patients (FIG. 8b) and 68 healthy Swedish blood donors (FIG. 8c). Background levels of healthy control sera are given to the left in the figures (open circles) and mean values are given. The OD405 nm levels are plotted for each individual.

Figure 9:
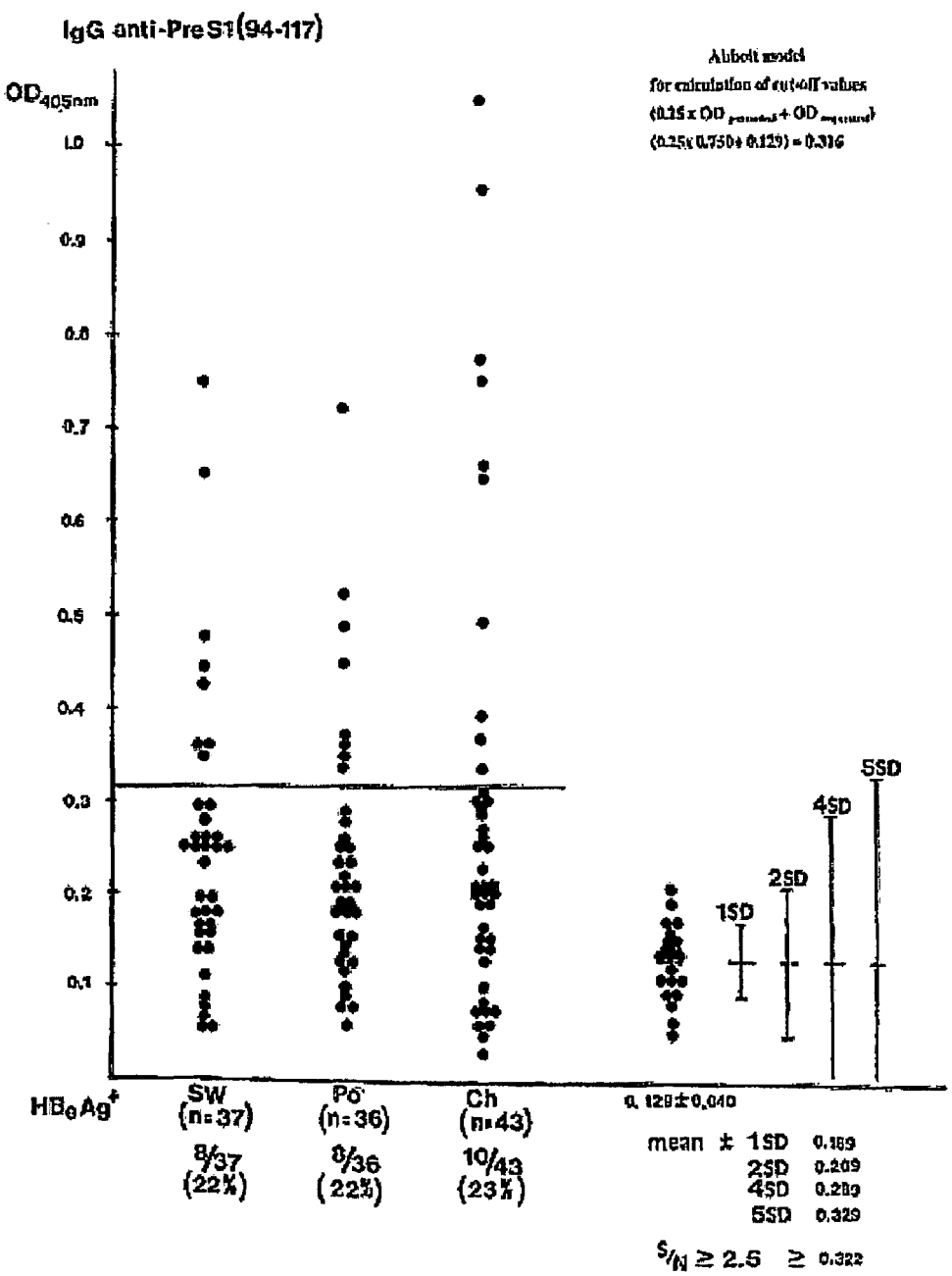

FIG. 9 shows the results of screening cohorts of 37 HBeAg$^+$ Swedish adults, 36 HBeAg$^+$ Polish children and 43 HBeAg$^+$ Chinese adults. The IgG anti-preS1(94-117) reactivity are compared to that of control sera to the right of the figure.

Figure 10:
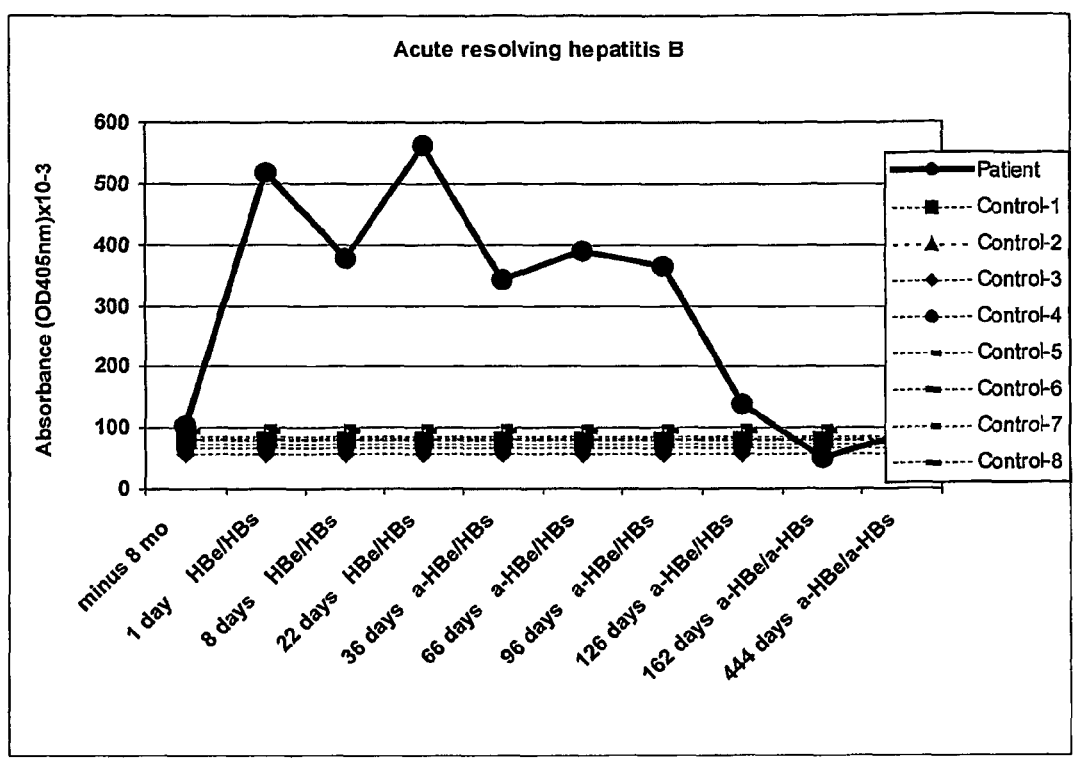

FIG. 10 shows the results of analysis of serum samples from one patient with acute resolving HBV-infection which were consecutively tested before and during acute infection. The X-axis gives the time schedule (days before and after onset of clinical symptoms). The solid line gives the IgG anti-preS1 (94-117) reactivity.

Figure 11:
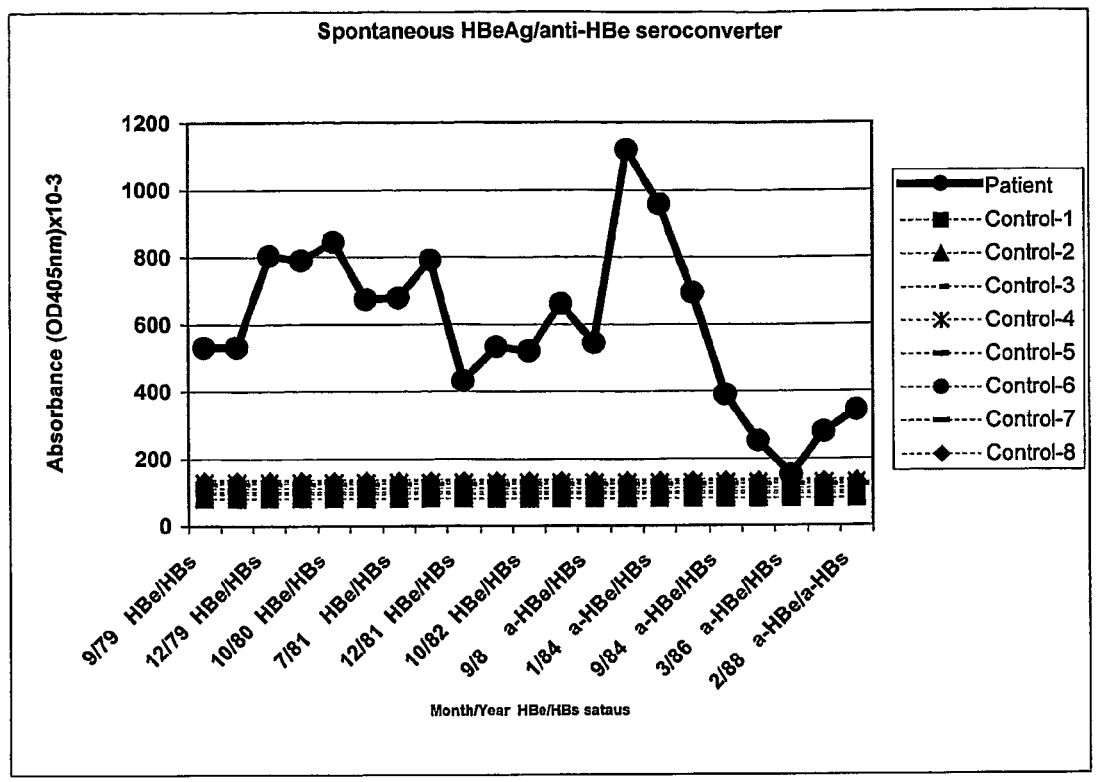

FIG. 11 shows demonstrates the IgG anti-preS1 (94-117) reactivity in serum samples consecutively collected during a 10 year time year during which the patient with chronic HBV-infection spontaneously seroconvert from HBeAg to anti-HBe reactivity (after 5 years of follow-up) and after 10 years follow-up from HBsAg to anti-HBs reactivity.

Figure 12A:
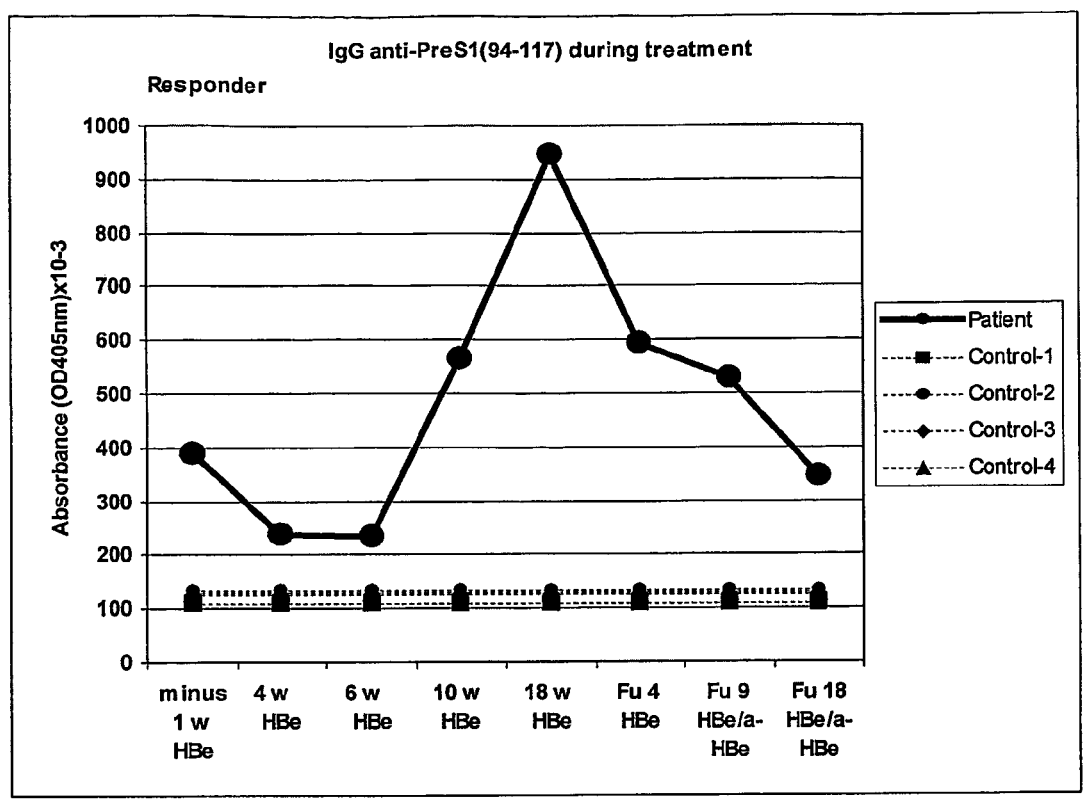
Figure 12B:
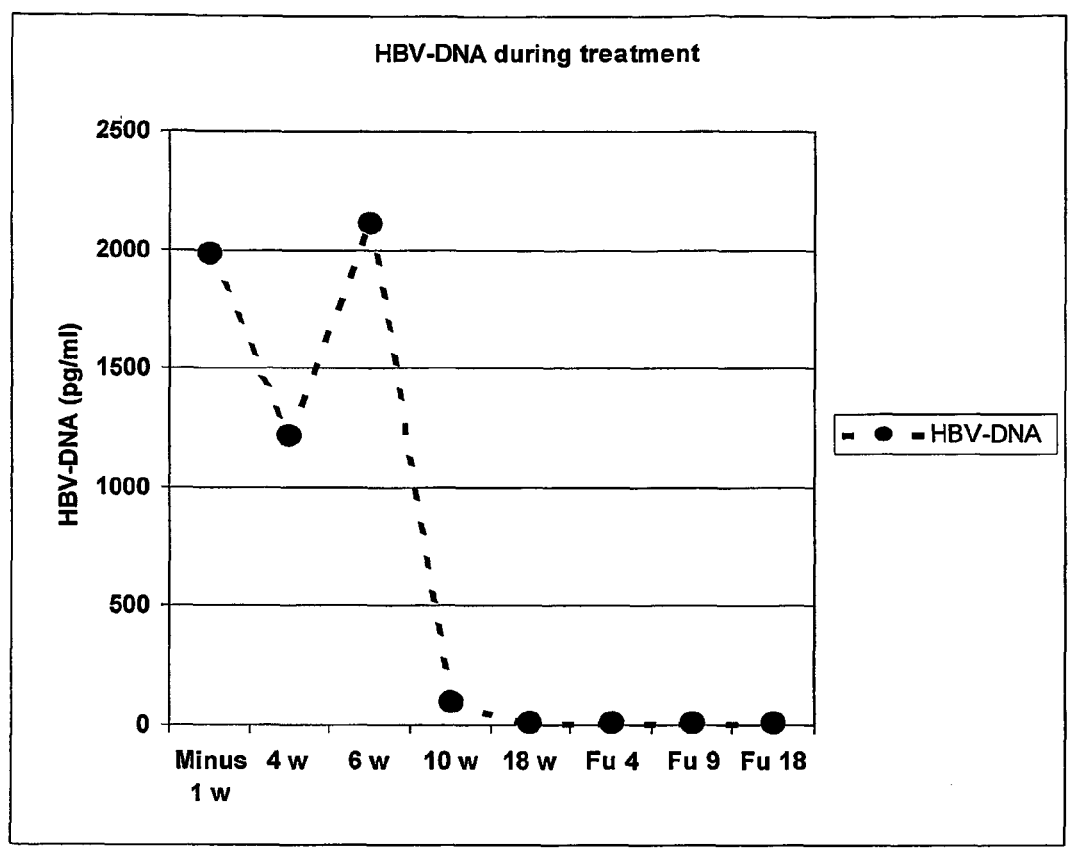

FIG. 12a shows Kinetic responses of IgG anti-preS1 (94-117) reactivity for one responder patient treated with alpha-IFN (Wellferm) for 20 weeks. Serum samples were collected before, during and after treatment and analyzed for anti-preS1 reactivity (I solid line) and HBV-DNA (I dotted line) (FIG. 12b). The background level in the ELISA plates with a pool (n=20) of healthy control sera are given by the dotted line (control 1-4).

FIG. 12b shows the level of HBV-DNA in the pretreatment serum from the responder patient.

Figure 13A:
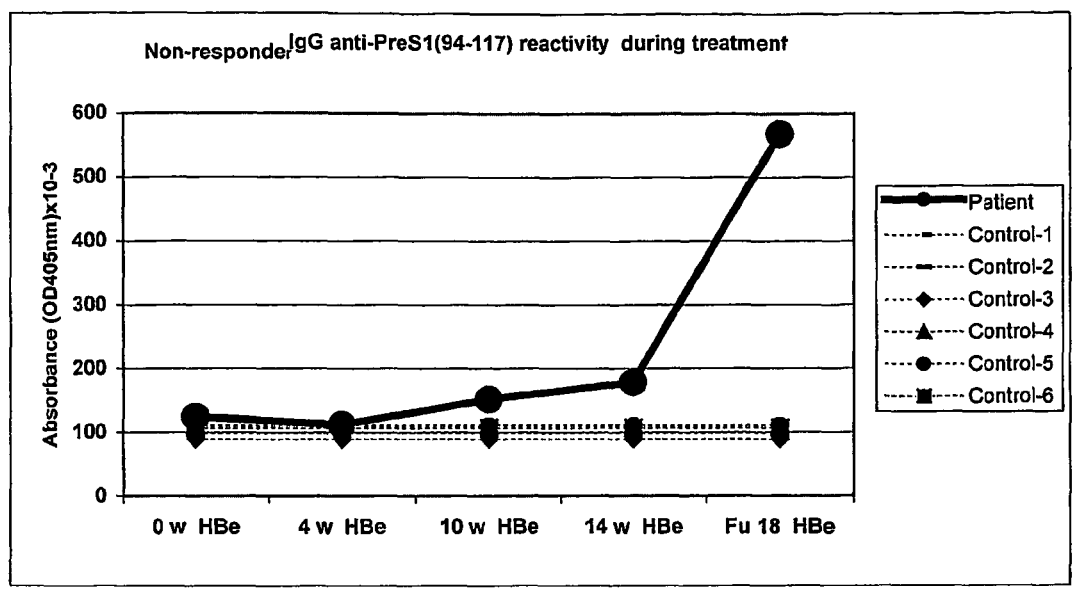

FIG. 13a shows kinetic responses of IgG anti-preS1 (94-117) reactivity for one non-responder (FIG. 13a) patient treated with alpha-IFN (Wellferm) for 20 weeks. Serum samples were collected before, during and after treatment and analyzed for anti-preS1 reactivity (I solid line, OD 405 nm)) and HBV-DNA (I dotted line, pg/ml) (FIG. 12b). The background level in the ELISA plates with a pool (n=20) of healthy control sera are given by the dotted line (control 1-4).

Figure 13B:
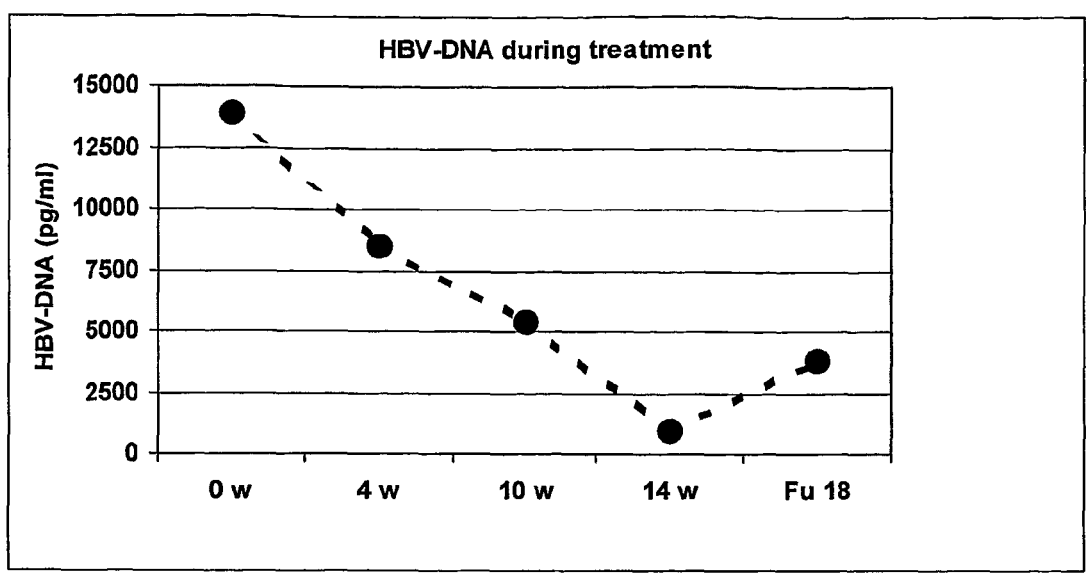

FIG. 13b shows the level of HBV-DNA in the pretreatment serum from the non-responder patient.

Figure 14A:
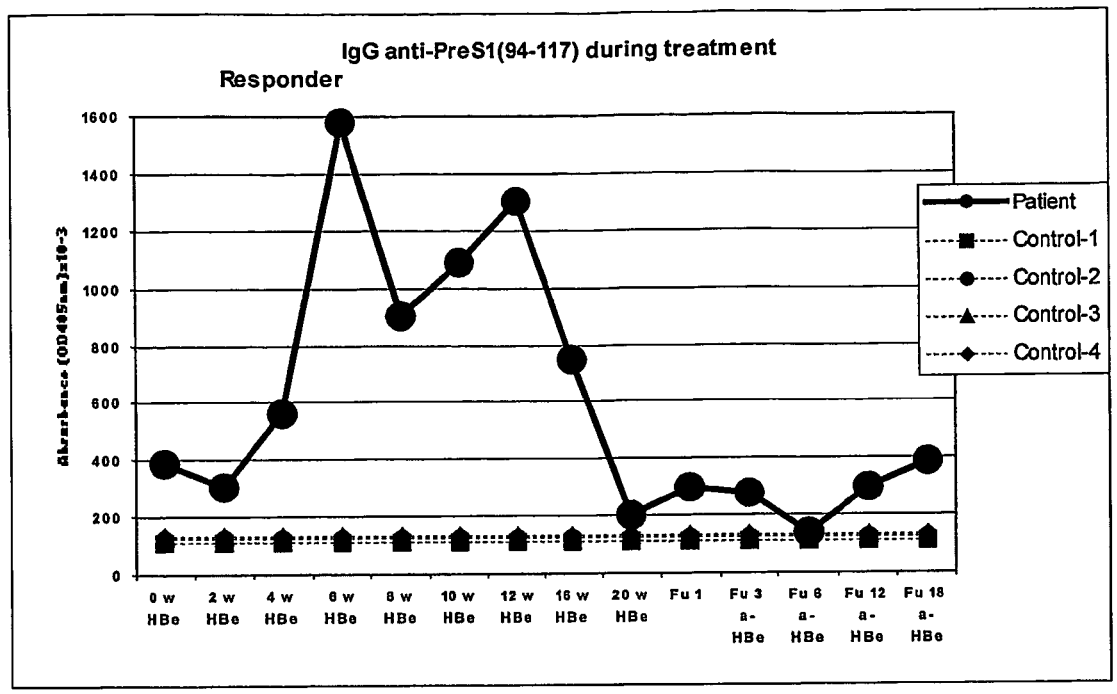

FIG. 14a shows kinetic responses of IgG anti-preS1 (94-117) reactivity for one responder patient depicted before, during and after treatment with prednisone and alpha-IFN. The solid line gives the OD values at 405 nm for the anti-preS1 reactivity.

Figure 14B:
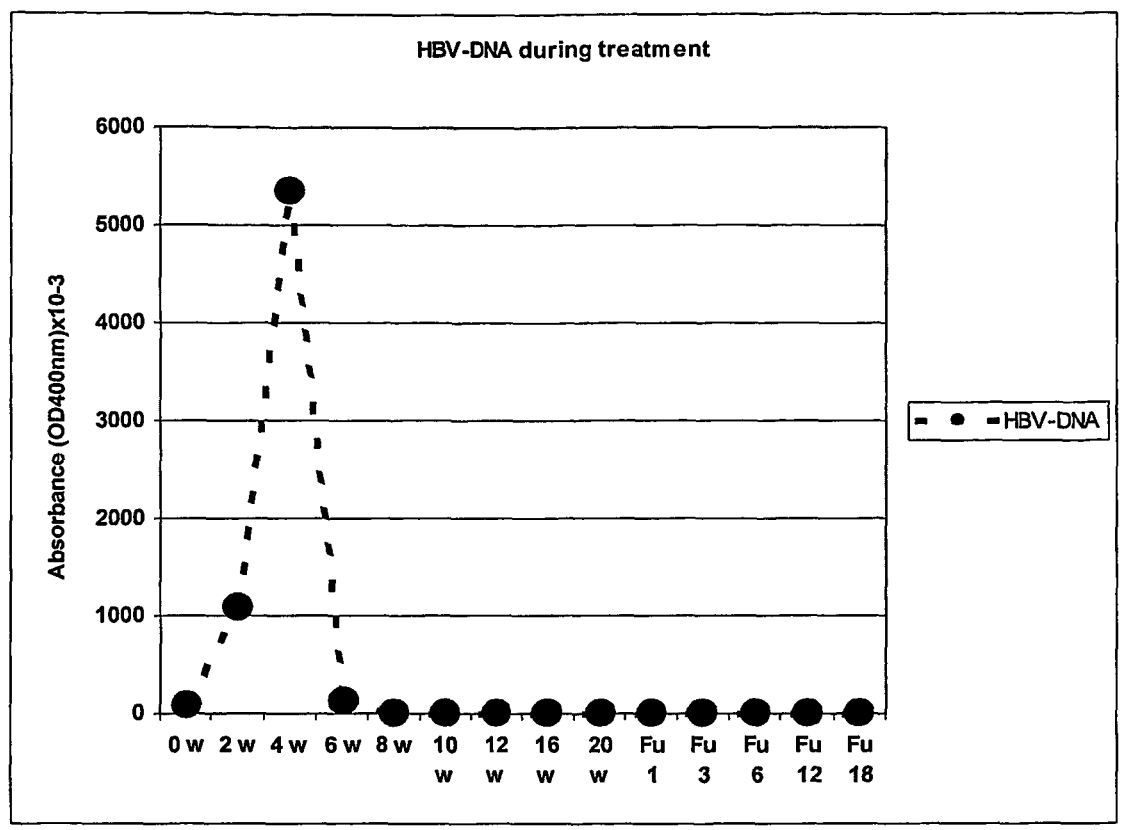

FIG. 14b shows serum HBV levels for the responder patient. The dotted line gives the result of quantitative measurements of serum HBV-DNA (pg/ml).

Figure 15A:
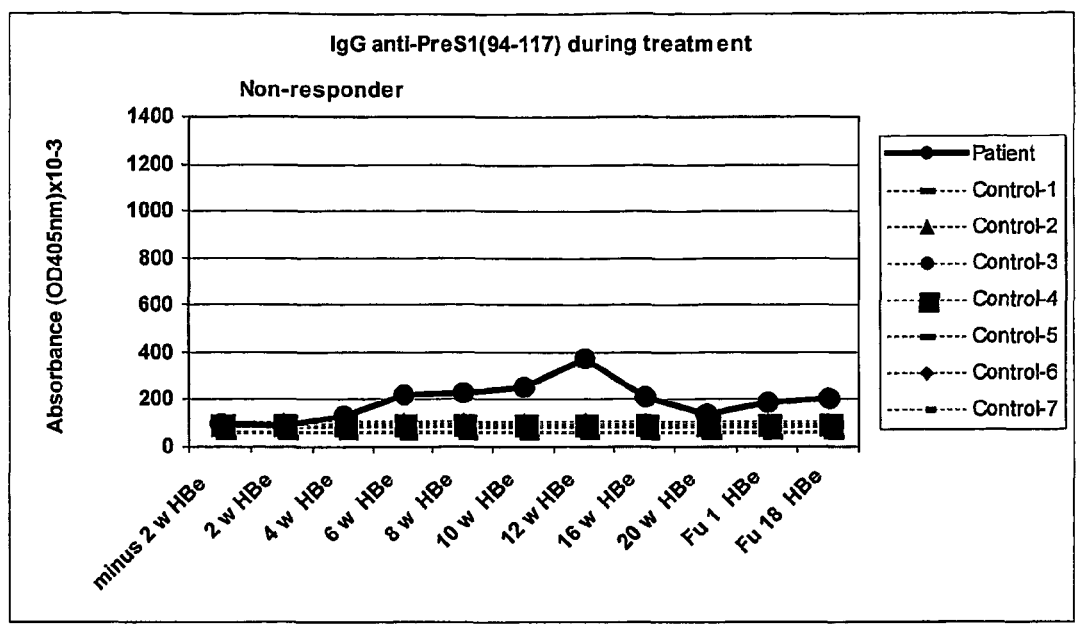

FIG. 15a shows kinetic responses of IgG anti-preS1 (94-117) reactivity for one non-responder patient depicted before, during and after treatment with prednisone and alpha-IFN. The solid line gives the OD values at 405 nm for the anti-preS1 reactivity.

Figure 15B:
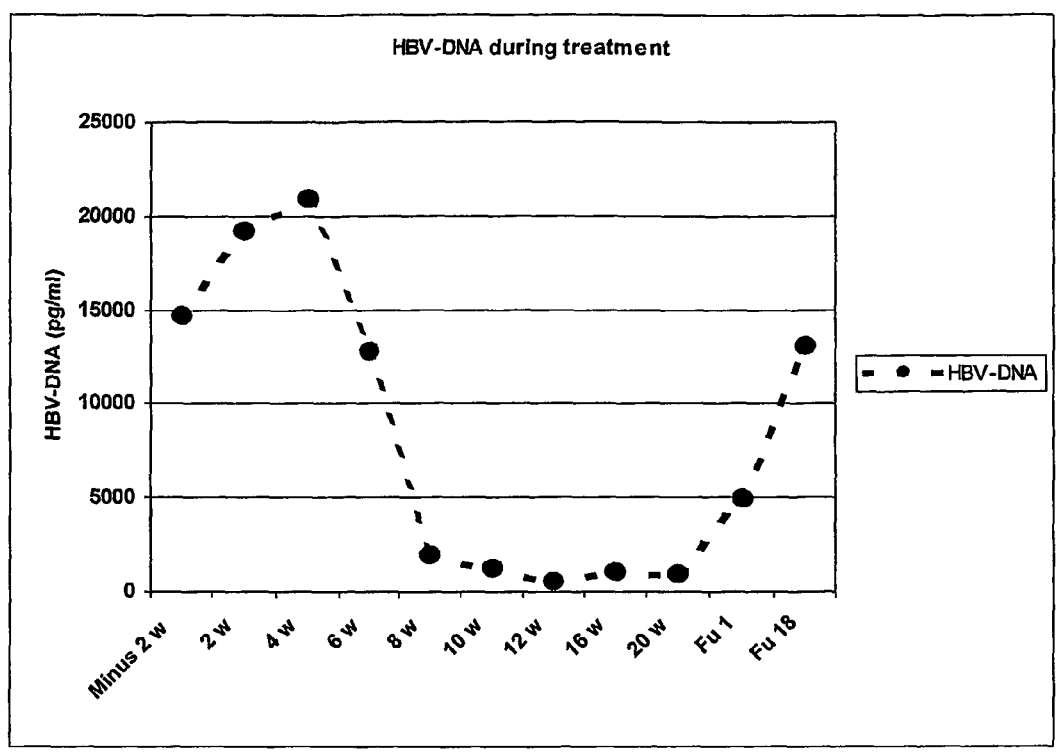

FIG. 15b shows kinetic responses of serum HBV-DNA levels. The dotted line gives the result of quantitative measurements of serum HBV-DNA (pg/ml).

Table 1 shows comparisons of the present methods for predicting response to IFN-alpha therapy compared to previously reported methods.

Table 2 shows the results of screening HBV patients using the present methods prior to IFN treatment.

Table 3 shows further results of screening HBV patients using the present methods prior to IFN treatment.

EXAMPLES

IgG anti-preS1#94-117 ELISA

Peptide:

A peptide consisting of the preS1#94-117 sequence of the HBV subtypes adw, adw$_2$ and two out of three described adr subtypes (i.e. PASTNRQSGRQPTPISPPLRDSHP) (SEQ ID NO:4) were obtained from Sigma Genosys, London Road, Cambridge, UK. The peptide was supplied lyophilized, resuspended in sterile distilled water and kept at −20° C. The purity was >95% by HPLC.

ELISA Plates:

Microtiter plates; Immunolon 2, flat bottom plates Catalog No. 011-010-3455 were obtained from Dynatech Laboratories Inc., Chantilly, Va., USA through the Swedish agency In vitro Sweden AB, Stockholm.

Coating Buffer:

0.05 M sodium carbonate buffer, pH 9.6 [1.59 g Na$_2$CO$_3$ (Catalogue No S-2127, min99%, Sigma-Aldrich) and 2.93 g NaHCO$_3$ (Catalogue No S-8875 min 99.5%, Sigma-Aldrich) to 100 ml with distilled water] was used as coating buffer. The peptide was diluted to final concentrations of 500, 1000 and 2000 ng/ml. In another test series, the final concentrations were 800, 1600 and 3200 ng/ml. For screening procedures, a final concentration of 2000 ng/ml was used throughout the studies. Fifty μl was added/well.

Coating Procedure:

For optimal coating, the plates were charged by incubation at 40° C. for 4 hours and thereafter stored in refrigerator at 4° C. overnight before use.

Figure 1A:
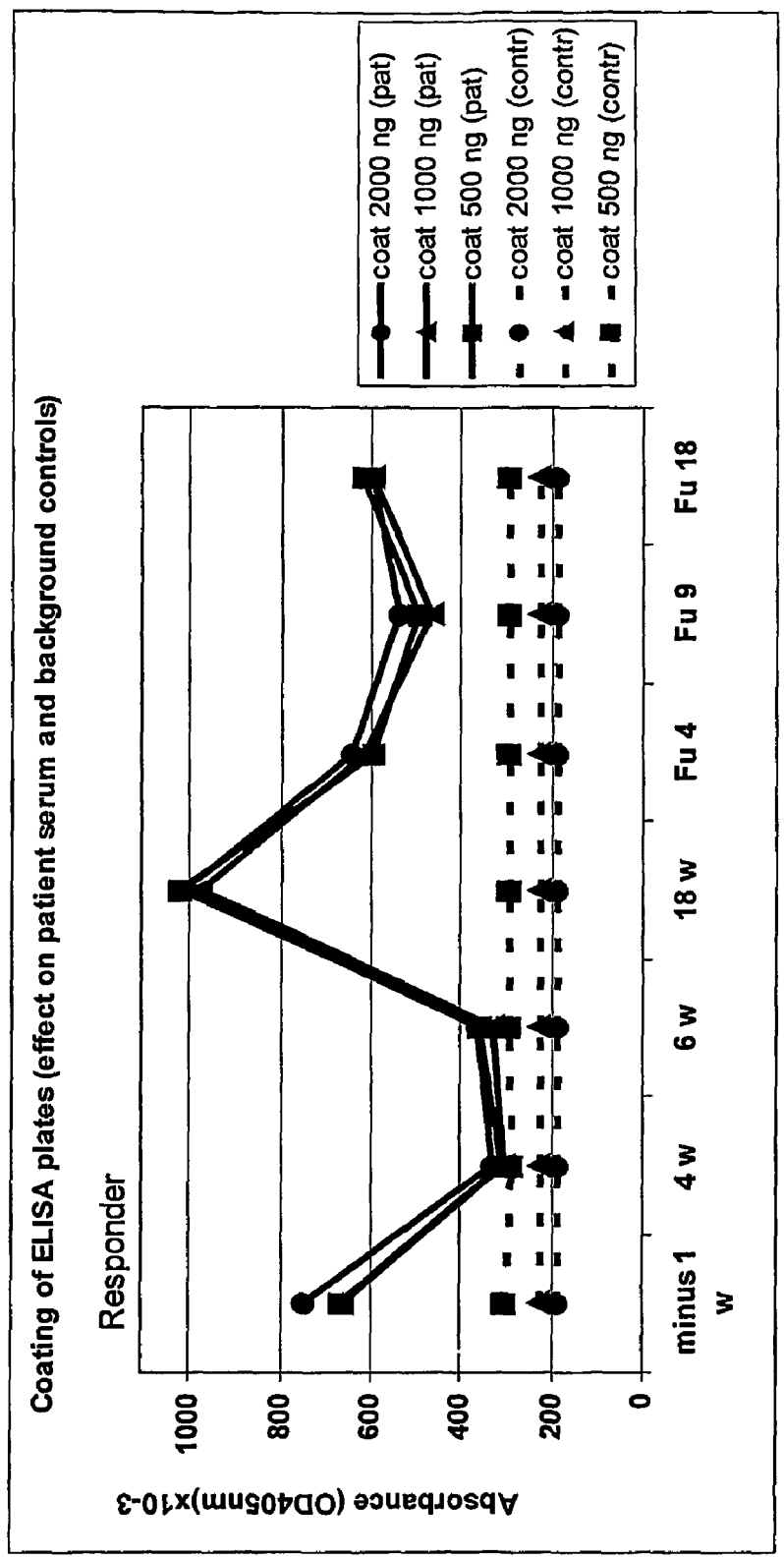
FIG. 1a shows an ELISA with serum samples from one responder at a range of peptide concentrations.

Throughout the screening procedure described herein, plates were stored overnight at 4° C. before used in the assay (FIG. 1A).

Washing of ELISA Plates

After each of the steps: 1) coating of plates, 2) incubation with patient- or control-sera, 3) incubation with conjugate, the plates were washed with 0.05 M NaCl (Catalogue No S-7653, SigmaUltra min 99.5%, Sigma-Aldrich) with 0.05% Tween.

Plates were washed three times by hand (e.g. without automated washing) with incubations of 5-10 minutes each time.

Incubation with Patient Sera:

Patient sera were diluted 1/125 for screening procedures or in two-step dilutions from 1/125 to 1/16 000 for titration experiments in 0.05 M phosphate-buffered saline (PBS) containing 0.05% Tween 20 (Polyoxyethylenesorbitan Monolaurate, Catalogue No P-1379, Sigma-Aldrich Sweden AB) and 1% Foetal bovine serum (FBS, heat-inactivated 56° C. 90 minutes) (catalogue No 10106-151 Gibco BRL, Life Technologies). Diluted sera (50 μl/well) were incubated at plates 4° C. overnight. (Shorter incubation time periods was not analyzed for during this set of experiments). The protein content in the dilution reagent is of importance and 1% FBS have earlier been found to be optimal during this type of "site-specific" ELISA systems.

Incubation with Conjugate:

Anti-human IgG conjugate: Affinity isolated antibodies to human IgG (gamma-chains specific) from goat labelled with alkaline phosphatase was used (Catalogue No A-3187, Sigma Aldrich).

The conjugate was diluted 1/1000 in PBS containing 0.05% Tween and 1% FBS and incubated on plates at 4° C. overnight.

Substrate:

p-nitrophenyl phosphate in diethanolamine HCl was used as substrate: Sigma 104 phosphatase substrate (p-Nitrophenyl phosphate, disodium, hexahydrate) 5 mg tablets was dissolved in 5 ml diethanolamine HCl, pH 9.8 [97 ml diethanolamine (Catalogue No D-8885 min 98%), 101 mg $MgCl_2 6H_2O$ (Catalogue No M-0250,Magnesium Chloride, Hexahydrate, Sigma-Aldrich) and approx. 160 ml 1 M HCl (Hydrochloric acid, 1 mol/l, Riedel-de Haén, 35328, Sigma-Aldrich 01780) in 1000 ml distilled water to get pH 9.8].

Reading of Plates:

The optical density (OD) value at 405 nm was measured in a TITERTEK Multiskan Plus Photometer (Flow Laboratories, Edinburgh, Scotland) after incubations for different time periods varying between 5-60 minutes. At optimal conditions plates was read after 20-30 minutes of incubation.

Normal (N) Values:

Sera from twenty healthy blood donors were pooled and used as control sera (n=20).

For screening purposes of unknown patient sera it is important that the different control sera tested negative for IgG, IgM and IgA anti-hepatitis (A, B, C, D and E) markers. The control sera were tested in commercially available test systems from Abbott Laboratories. Sera with reactivity within the grey zone 10-20% ±the cut-off value were avoided.

During these assay conditions the mean OD 405 value for control (n=20) sera±5 SD was equivalent to sample (S) over normal (N) values (S/N)≧2.5.

Patient Sera with Positive Reactivity

For screening procedures patient and control sera were diluted 1/125 and assayed for reactivity. S/N values≧2.5 were considered positive.

Titers of Sera: Both patient- and control-sera were diluted from 1/125 to 1/16 000 and assayed for reactivity. The endpoint for positive reactivity could thereafter be found.

Inhibition Experiments:

Equal volumes of diluted (PBS-Tween-1% FBS) patient sera and inhibitor (PBS-Tween-1% FBS) were incubated for 4 hours at 4° C. and thereafter transferred to coated ELISA plates, followed by the procedure described above.

Inhibitory reagents used: preS1#94-117, preS1#21-32, preS1#11-117, preS1#21-47.

Statistics:

The non-parametric Mann-Whitney U test was employed to compare data between groups of patients.

The Chi-squared test was used to compare number of reactive individuals in different group of patients when the individuals in the groups were ≧5.

The Fischer's exact test was used when the patient groups were smaller than 5.

Optimal Concentration of the Peptide Protein for Charge of the Solid Phase (eg ELISA Plates).

The solid phase (i.e. ELISA plates) were charged with 500, 1000 or 2000 ng peptide/ml. Serum samples from one responder (FIG. 1a) and one non-responder (FIG. 1b) HBeAg-reactive patient (solid line) were compared with a pool (n=20) of "healthy" control sera (dotted lines). Sera were diluted 1/125 and analysed for IgG anti-preS1 (94-117) reactivity. OD values at 405 nm are given.

For the responder patient (Swedish adult), the serum samples were collected before (−1 week), during (4, 6 and 18 weeks) and after (4, 9 and 18 months) treatment with alpha-IFN (Wellferm) for 20 weeks (FIG. 1a)

Figure 1B:
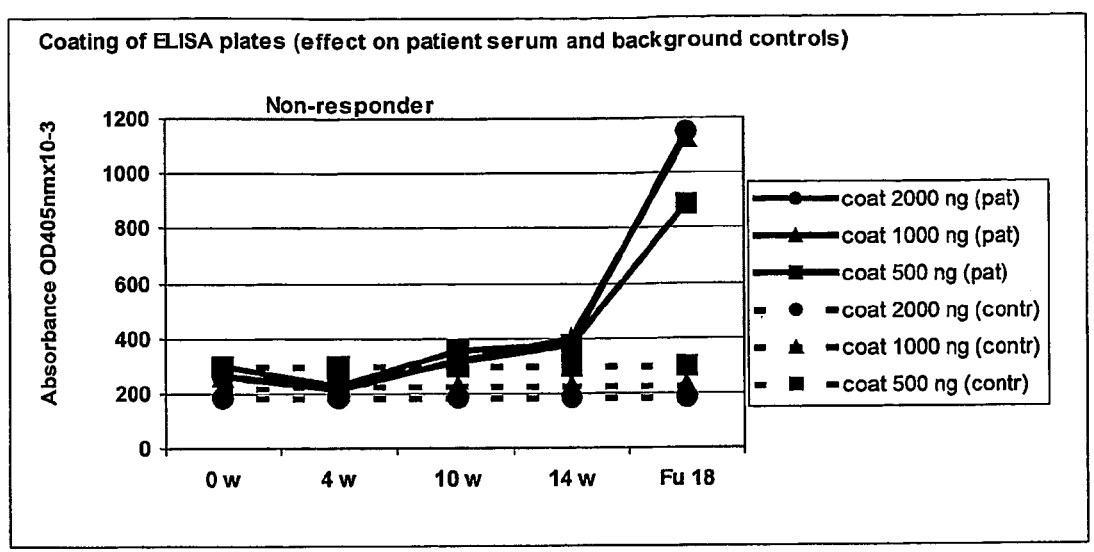
FIG. 1b shows an ELISA with serum samples from one non-responder at a range of peptide concentrations.

For the non-responder patient (Swedish adult), the serum samples were collected before (time 0), during (4, 10 and 14 weeks) and after (18 months) of treatment (FIG. 1b).

The responder patient had an IgG anti-preS1 (94-117) reactive pretreatment serum, while the pretreatment serum from the non-responder patient lacked detectable levels of anti-preS1 antibodies.

The 200 ng/ml coat of plates gave the lowest background level. A charge of the solid phase of 2000 ng/ml of the preS1 (94-117) peptide was thereafter used throughout the study for screening procedures.

Reproducibility

Figure 2:
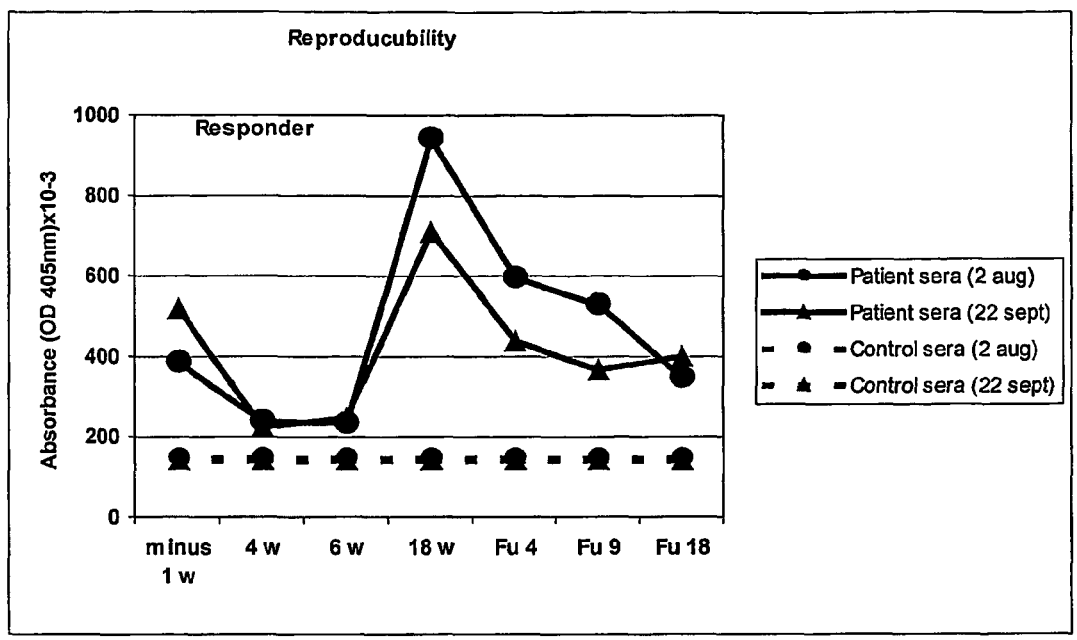
FIG. 2 shows ELISA data indicating the reproducibility of the test system.

The reproducibility of the test system is shown in FIG. 2. The reactivity is given for the responder patient discussed above when the same serum samples were tested one month apart.

The Curve Profile of IgG Anti-preS1 (94-117) Reactive Patient Sera in the Assay System.

Figure 3:
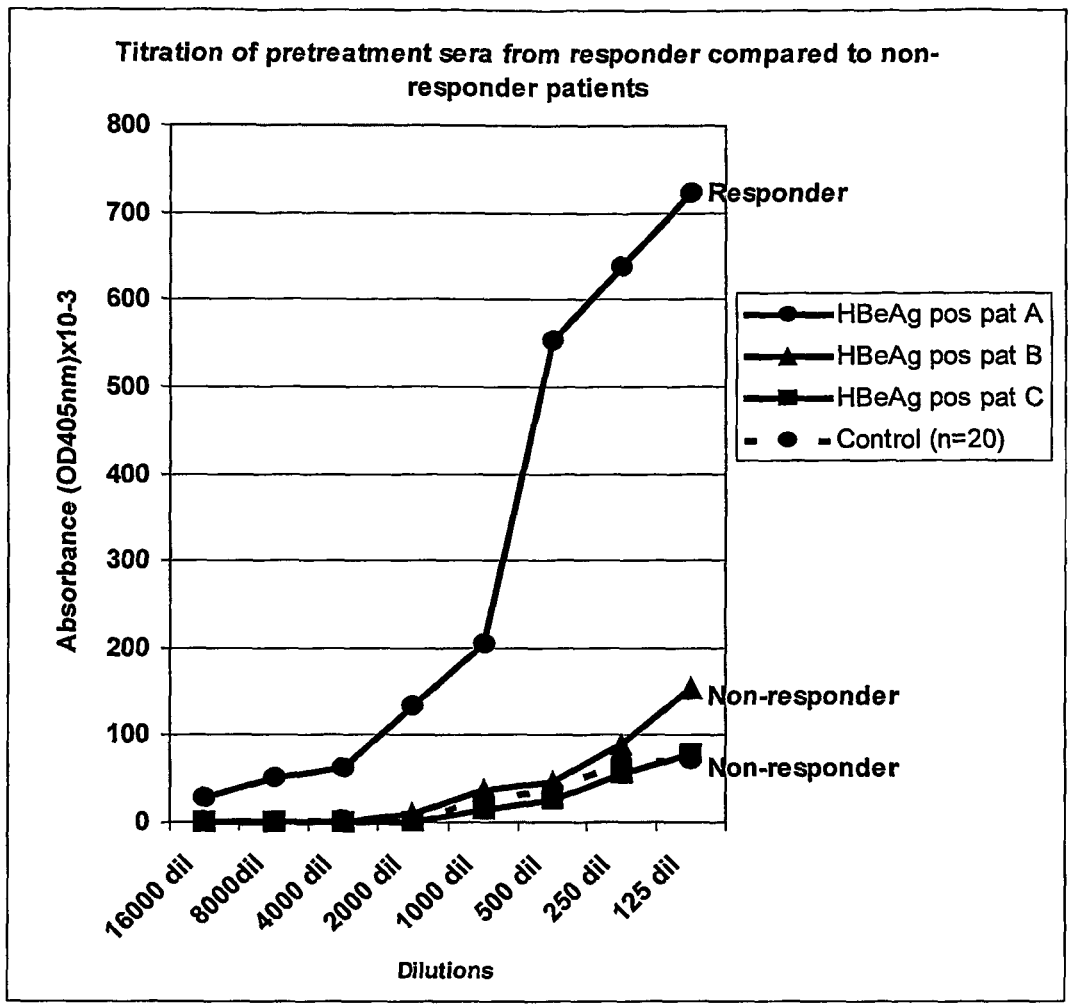
FIG. 3 shows results of analysis of pretreatment sera from three HBeAg+ Polish children (one responder and two non-responders, solid lines) tested for IgG anti-preS1 (94-117) reactivity and compared with a pool (n=20) of healthy control individuals (dotted line)

Pretreatment sera from three $HBeAg^+$ Polish children (one responder and two non-responders, solid lines) were tested for IgG anti-preS1 (94-117) reactivity and compared with a pool (n=20) of healthy control individuals (dotted line)(FIG. 3) Sera were diluted two-stepwise from 1/125 to 1/16 000 and data presented as OD values at 405 nm).

The pretreatment responder patient serum (●) contained high titers (end point 4000) of IgG anti-preS1 (94-117) compared to the two pretreatment sera from non-responder patients (▲ and ■) which were negative.

Figure 4:
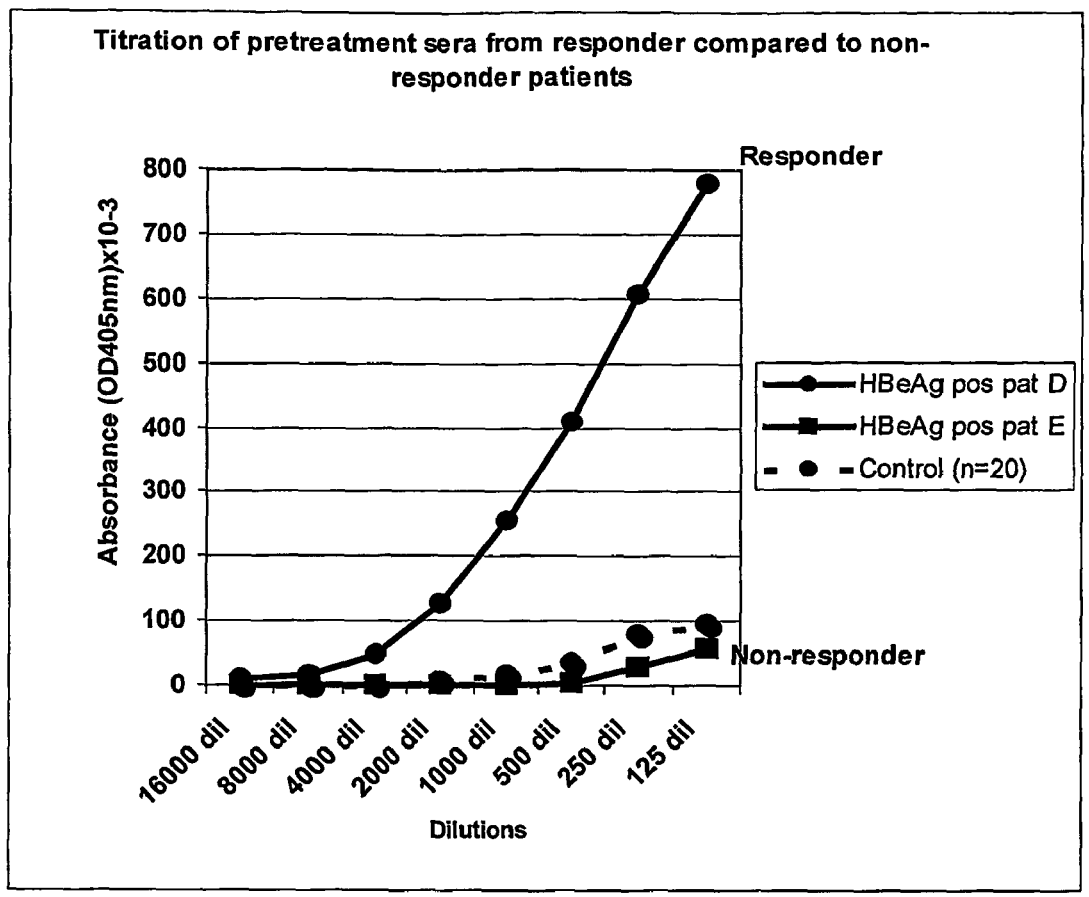
FIG. 4 shows the reactivity of pretreatment sera from one responder (λ) and one non-responder (v) HBeAg+ Swedish adult patient.

FIG. 4 demonstrates the reactivity of pretreatment sera from one responder (●) and one non-responder (■) $HBeAg^+$ Swedish adult patient.

The pretreatment serum from the responder patient was positive with a high titer (2000) of IgG anti-preS1 (94-117) antibodies, while the pretreatment serum from the non-responder lacked detectable levels of antibodies.

Specificity of the IgG anti-preS1 (94-117) ELISA.

Inhibition of IgG Anti-preS1 (94-117) Reactivity.

Serum from one HBeAg+ patient (FIG. 5a) with chronic HBV-infection, who later spontaneously seroconverted to anti-HBe reactivity and three HBeAg+ patients with acute resolving HB-infection (FIGS. 5b, 6a and 6b) were incubated with incubation buffer instead of inhibitor (▲ dotted line), preS1 (94-117) (● solid line) or preS1 (21-32)(■ dotted line) before addition to preS1 (94-117) coated ELISA plates. Data are given as OD values at 405 nm.

The soluble preS1 (94-117) peptide inhibited the IgG anti-preS1 (94-117) reactivity to 100%, while the preS1 peptide (21-32) from the N-terminal part of preS1 did not.

Serum from a HBeAg+ chronic patient was preincubated with preS1 (94-117, ●), the whole preS1 (11-117, ▲) or the preS1 sequence(21-47, ■) corresponding to the so called hepatocyte receptor (n)(FIG. 7).

The soluble preS1 (94-117) peptide inhibited the IgG anti-preS1 (94-117) reactivity to 100%. While the irrelevant preS1 peptides did not.

Sensitivity of the IgG Anti-preS1 (94-117) ELISA at Different Follow-up Times

Twelve out of 13 (92%) $HBeAg^+$ patients responded to treatment with alpha-IFN alone or in combination with prednisone when followed 12 (Fu 12) up to 18 (Fu 18) months after end of treatment (Table 2). Response was judged by the elimination of viral replication as assessed by quantitative measurements of serum HBV-DNA and/or seroconversion from HBeAg to anti-HBe reactivity.

The responder patient who is classified in the Table 2 as negative had a borderline reactivity and was positive in some, but negative in other experiments. The reactivity pattern of this patient may be retested with more serum samples.

In contrast all non-responder patients (0/9, 0%) lacked detectable levels of IgG anti-preS1 (94-117) (Table 3). The difference in IgG anti-preS1 (94-117) reactivity between responder and non-responder patients is significant ($p<0.0005$).

For another set of HBeAg+ patients followed 1, 2, 3 or 6 months after treatment (Tables 2 and 3) 6/7 (86%) responder patients compared to 0/13 (0%) non-responder patients ($p<0.0005$) had pretreatment samples with detectable levels of IgG anti-preS1 (94-117).

The IgM anti-preS1 (94-117) reactivity in pretreatment did not differ significantly between responder and non-responder patients (Tables 2 and 3).

Comparison with Other Predictive Markers.

Pretreatment samples from responder compared to non-responder patients were also analysed for content of IgM anti-HBc (Sample/Cut-off, S/CO), transaminases (ALT, µkat/L), serum HBV-DNA (pg/ml) and histology (CPH or CAH) (Tables 2 and 3). These parameters have earlier been discussed in the context of search for predictive markers. For the patients tested in this study, no significant differences were found between the two groups of patients.

IgM and IgG antibodies with specificity for the first or the second part of the hepatocyte receptor; preS1 (12-32) or preS1 (32-47), did not differ significantly between responder and non-responder patients (Tables 2 and 3).

The IgG Anti-preS1 (94-117) Reactivity in Sera from a Cohort of HBeAg Reactive Sera from Patients (Swedish, Polish and Chinese) with Chronic HBV-infection.

For screening, patient and control seras were diluted 1/125. Results from three different experiments are depicted in FIG. 8 a-c. Background levels of healthy control sera are given to the left in the figures (open circles) and mean values are given. The OD405 nm levels are plotted for each individual in a cohort of 24 Chinese HBeAg+ patients (FIG. 8a), 17 Swedish HBeAg+ patients (FIG. 8b) and 68 healthy Swedish blood donors (FIG. 8c).

In another set of experiments (FIG. 9) the OD values at 405 nm are plotted for each individual in cohorts of 37 HBeAg+ Swedish adults, 36 HBeAg+ Polish children and 43 HBeAg+ Chinese adults. The IgG anti-preS1 (94-117) reactivity are compared to that of control sera to the right of the figure.

Sample (S) over normal (N) values>2.5 are judged as the cut-off value for positive reactivity. It equals a mean control value ±5-6 SD.

A cohort of HBeAg+ patients (22-25%) have detectable levels of IgG anti-preS1 (94-117) in sera. The frequency of IgG anti-preS1(94-117) reactive sera from HBeAg+ patients were the same, irrespective of ethnical origin (eg Chinese or Swedish).

Kinetic Response of IgG anti-preS1 (94-117) Reactivity in Sera during Acute HBV-infection.

Serum samples from one patient with acute resolving HBV-infection were consecutively tested before and during acute infection (FIG. 10). The X-axis gives the time schedule (days before and after onset of clinical symptoms). The solid line gives the IgG anti-preS1 (94-117) reactivity. Serum samples were negative for IgG anti-preS1 (94-117) before but reactive after onset of clinical symptoms. The IgG anti-preS1 (94-117) reactivity peaked at the time for HBeAg/anti-HBe seroconversion (36 days) but declined at the time for HBsAg/anti-HBs seroconversion (162 days).

The dotted line gives the background values in the plates with a pool (n=20) of healthy control sera.

Kinetic Response of IgG anti-preS1 (94-117) Reactivity in a HBeAg Chronic Patient who Spontaneously Seroconvert to Anti-HBe and Later to Anti-HBs.

FIG. 11 demonstrates the IgG anti-preS1 (94-117) reactivity in serum samples consecutively collected during a 10 year time period during which the patient with chronic HBV-infection spontaneously seroconverted from HBeAg to anti-HBe reactivity (after 5 years of follow-up; month/year 4/83) and after 10 years follow-up (month/year 1/88) from HBsAg to anti-HBs reactivity. The serum IgG anti-preS1 (94-117) reactivity fluctuates during HBe-antigenimia, reaching peak levels after the seroconversion to anti-Hbe and declining during the time for seroconversion to anti-HBs reactivity.

Kinetic Responses of IgG Anti-preS1 (94-117) Reactivity During Treatment with Alpha-IFN in Responder Compared to Non-responder Patients.

Kinetic responses of IgG anti-preS1 (94-117) reactivity for one responder (FIG. 12a) and one non-responder (FIG. 13a) patient treated with alpha-IFN (Wellferm) for 20 weeks. Serum samples were collected before, during and after treatment and analyzed for anti-preS1 reactivity (solid line) (FIGS. 12a and 13a) and HBV-DNA (dotted line, pg/ml) (FIGS. 12b and 13b). The background level in the ELISA plates with a pool (n=20) of healthy control sera are given by the dotted line (control 1-4).

The pretreatment serum from the responder patient contained anti-preS1 antibodies and HBV-DNA (FIGS. 12a and 12b), while the pretreatment serum from the non-responder patient had high levels of HBV-DNA but lacked detectable levels of IgG anti-preS1(94-117) (FIGS. 13a and 13b).

The presence of serum antibodies with specificity for the N-terminal part of preS1 is dynamic and is fluctuating during the treatment schedule. For the responder patient, the reactivity reached a peak at the time for seroconversion from HBeAg to anti-HBe reactivity.

Kinetic Responses of IgG Anti-preS1 (94-117) Reactivity During Combined Prednisone, Alpha-IFN Treatment.

Kinetic responses of IgG anti-preS1 (94-117) reactivity for one responder (FIG. 14a) and one non-responder (FIG. 15a) patient are depicted before, during and after treatment with prednisone and alpha-IFN. The solid line gives the OD values at 405 nm for the anti-preS1 reactivity (FIGS. 14a and 15a) and the dotted line the result of quantitative measurements of serum HBV-DNA (pg/ml) (FIGS. 14b and 15b). Positive pretreatment levels of anti-preS1 for the responder patient (FIG. 14a).

The predictive marker is valid both for alpha-IFN treatment with or without combined treatment with prednisolone.

Comparison with Known Predictive Markers

Predicted response to IFN-alpha therapy based on pretreatment data has previously been studied by the use of various statistical models.

Lau et al, 1998 *Journal of Viral Hepatitis* 5: 105-114 gave the arbitrary prediction to be 33% responders and 67% non-responders, see Table 1. By the use of a two-stage logistic model with pretreatment variables (sex, hepatic fibrosis, ALT levels) they increased the number of responders from 33% to 61% (e.g. the sensitivity and non-responders from 67% to 76% (e.g. the specificity).By Smiles logistic regression the numbers of responders to non-responders increased to 77% and 87%, respectively.

Brook et al, 1989 *Hepatology* 10: 761-763 increased the sensitivity from 33 to 77% and the specificity from 67 to 79% by the use of pretreatment variables AST levels and history of acute hepatitis.

Perillo et al, 1993 *Hepatology* 18: 1306-1312 used stepwise Cox regression analysis with pretreatment variables HBeAg and ALT levels. The sensitivity and the specificity was raised to 81% and 46% respectively.

Lindh et al and Söderström et al used the pretreatment variable HBV-DNA (<500 million copies/ml and 160 million copies/ml, respectively). The sensitivity was 51% and 67%, respectively and the specificity 74% and 89%, respectively. The first group (Lindh et al) treated adults, while the latter group (Söderström, et al) treated children with a combined regime The data obtained from the non-invasive assay described herein shows that the sensitivity was raised from 33% to 92% and the specificity from 67% to 100%, with a follow-up 12-18 months (Table 1 and 2).

TABLE 1

|  | Responders | Non-responders |
|---|---|---|
| Arbitrary prediction | 33% | 67% |
|  | Sensitivity | Specificity |
| Lau et al, 1998<br>The two-stage logistic model using<br>Pretreatment variables (sex, hepatic<br>Fibrosis and ALT levels) | 61% | 76% |
| Smiles logistic regression<br>Incorporates interactions between<br>the parameters | 77% | 87% |
| Brook et al, 1989<br>Pretreatment variables (AST<br>levels and history of acute<br>hepatitis) | 77% | 79% |
| Perillo et al, 1993<br>Stepwise Cox regression analysis<br>(pretreatment variables HBeAg<br>concentrations and ALT levels) | 81% | 46% |
| Lindh et al, 2001 (combined therapy)<br>Pretreatment variable HBV-DNA<br>(<500 million copies/ml) | 51% | 74% |
| Söderström et al, 2003<br>(combined therapy, children)<br>Pretreatment variable HBV-DNA<br>(160 million copies/ml) | 67% | 89% |
| Hellström and Sylvan (New data)<br>Presence of IgG anti-preS1(94-117)<br>antibodies in pretreatment sera)<br>Follow-up time 12-18 months | 92% | 100% |

Lau et al (Journal of Viral Hepatitis 5: 105-114, 1998)
Brook et al (Hepatology 10: 761-763, 1989)
Perillo et al (Hepatology 18: 1306-1312, 1993)
Lindh et al (Journal of Viral Hepatitis 8: 349-357, 2001)
Söderström et al, 2003 (Thesis)

RESPONDER PATIENTS
Pretreatment anti-PreS1 markers

| OreS1 Name | Age | Sex | Treatm | Follow-up | IgG anti-preS1 21-32 | 32-47 | 94-117 | IgM anti-p 21-32 | 32-47 | 94-117 | IgM a-HBc | ALT | HBV-DNA | Hist |
|---|---|---|---|---|---|---|---|---|---|---|---|---|---|---|
| 2442 | Sw adult | M | IFN | Fu 18 | neg | pos | pos | pos | pos | pos | 2.3 | 58 | 1981 |  |
| 2461 | Sw adult | M | IFN | Fu 18 | neg | neg | pos | pos | pos | pos | 0.6 | 33 | 2690 |  |
| 2421 | Sw adult | M | IFN | Fu 18 | pos | pos | pos | neg | neg | neg | 1.5 | 66 | 691 |  |
| 2482* | Sw adult | M | IFN | Fu 18 | neg | neg | neg* | neg | neg | neg | 2.2 | 54 | 5353 |  |
| Kanafek | Po 2 ¼ | M | IFN | Fu 18 | pos | pos | pos | pos | pos | pos | 0.6 |  | 610 | CAH |
| alpha-10 | Ch 35 | F | ST/IFN | Fu 18 | pos | pos | pos | pos | pos | pos | 1.5 |  | 77 | CAH |
| Dziewa | Po 5 ½ | F | ST/IFN | Fu 12 | pos | pos | pos | pos | pos | pos | 4.2 |  | 78 | CAH |
| 337 | Po 12 ½ | F | IFN | Fu 12 | pos | pos | pos | pos | pos | pos | 1.4 | 220 |  | CAH |
| 3211 | Po 4 | M | IFN | Fu 12 | pos | pos | pos | neg | pos | neg | 0.5 | 233 |  | CAH |
| 1950 | Po 5 5/12 | F | IFN | Fu 12 | pos | pos | pos | neg | neg | neg | 0.4 | 51 |  | CAH |
| 2090 | Po 5 | M | IFN | Fu 12 | pos | neg | pos | pos | pos | pos | 0.3 | 145 |  | CAH |
| 1017 | Po 4 | M | IFN | Fu 12 | pos | neg | pos | pos | pos | pos | 0.3 | 34 |  | CAH |
| 2324 | Pa 2 | M | IFN | Fu 12 | pos | pos | pos | pos | pos | pos | 1.9 | 450 |  | CAH |
| n = 13 |  |  |  |  | 10 pos | 9 pos | 12 pos | 9 pos | 10 pos | 9 pos | 1.4 ± 0.3 | 134 ± 42 | 1640 ± 721 | 9 CAH |
|  |  |  |  |  | 77% | 69% | 92% | 69% | 77% | 69% |  |  |  | 100% |
|  |  |  |  |  | a) | b) | c) | d) | e) | f) | g) | h) | i) | k) |

NON-RESPONDER PATIENTS
Pretreatment anti-PreSi markers

| Name | Age | Sex | Treatm | Follow-up | IgG anti-preS1 21-32 | 32-47 | 94-117 | IgM anti-preS1 21-32 | 32-47 | 94-117 | IgM a-HBc | ALT | HBV-DNA | Mist |
|---|---|---|---|---|---|---|---|---|---|---|---|---|---|---|
| 2462 | Sw adult | M | IFN | Fu 18 | neg | pos | neg | neg | neg | neg | 5.9 | 57 | 3064 |  |
| 2443 | Sw adult | M | IFN | Fu 18 | neg | pos | neg | neg | neg | neg | 2.1 | 57 | 13,880 |  |
| Suchan | Po 4 1/12 | M | IFN | Fu 18 | pos | pos | neg | neg | neg | neg | 1.9 |  | 160 | CAH |
| Dunczyk | Po 2 1/6 | M | ST/IFN | Fu 12 | pos | pos | neg | neg | neg | neg | 0.5 |  | 780 | CPH |
| Zyfert | Po 5 ⅔ | M | ST/IFN | Fu 12 | neg | pos | neg | pos | pos | pos | 0.8 |  | 550 | CAH |
| Gorbacz | Pp 6 ½ | M | ST/IFN | Fu 12 | pos | pos | neg | neg | neg | neg | 0.6 |  |  | CAH |
| 71 | Po 1 ⅓ | M | IFN | Fu 12 | pos | neg | neg | pos | pos | neg | 0.3 |  |  | CAH |
| 831 | Po 13 5/12 | F | IFN | Fu 12 | neg | neg | neg | neg | neg | neg | 0.4 | 136 |  | CAH |
| alpha-6 | Ch 33 | M | ST/IFN | Fu 12 | neg | neg | neg | neg | neg | neg | 0.5 | 136 |  | CAH |

-continued

|  |  |  |  |  |  |  |  |  |  |  |  |  |  |
|---|---|---|---|---|---|---|---|---|---|---|---|---|---|
| n = 9 |  |  |  | 4 pos | 5 pos | 0 pos | 3 pos | 2 pos | 1 pos | 1.4 ± 0.6 | 97 ± 23 | 3686 ± 2598 | 6 CAH |
|  |  |  |  | 44% | 56% | 0% | 33% | 22% | 11% |  |  |  | 86% |
|  |  |  |  | a) | b) | c) | d) | e) | f) | g) | h) | i) | k) |
|  |  |  |  | NS | NS |  | NS | NS | NS | NS | NS | NS | NS |
|  |  |  |  |  |  | p<0.0005 |  |  |  |  |  |  |  |

* pos sometimes/neg sometimes

TABLE 3

RESPONDER PATIENTS
Pretreatment anti-PreS1 markers

| Name | Age | Sex | Treatm | Follow-up | IgG anti-preS1 | | | IgM anti-preS1 | | | 1gM a-HBc | ALT | HBV-DNA | Hist |
|---|---|---|---|---|---|---|---|---|---|---|---|---|---|---|
|  |  |  |  |  | 21-32 | 32-41 | 94-111 | 21-32 | 32-47 | 94-117 |  |  |  |  |
| Kamineka | Po 1 y 9/12 | F | IFN | Fu 6 | pos | pos | pos | neg | pos | pos | 2.6 |  |  | CPH |
| Walasik | Po 12 1/12 | M | IFN | Fu 6 | pos | pos | pos | neg | pos | pos | 0.9 |  |  | CAH |
| 146 | Po 12 | M | IFN | Fu 6 | neg | neg | pos | neg | neg | pos | 0.4 | 126 |  | CPH |
| 2337 | Po 2 | M | IFN | Fu 6 | pos | pos | pos | pos | pos | neg | 1.9 |  |  | CAH |
| A3 | Ch 40 | F | IFN | Fu 6 | pos | pos | pos | pos | pos | pos | 1.1 | 67 | 708 | CAH |
| Zlotek* | Po 4 1/2 | M | ST/IFN | Fu 6 | pos | pos | neg* | neg | neg | neg | 1.1 |  |  | CAH |
| B1 | Ch 36 | M | IFN | Fu 3 | pos | neg | pos | neg | pos | neg | 0.5 | 195 | 246 | CAH |
| n = 7 |  |  |  |  | 6 Poe | 4 pos | 6 pos | 2 pos | 5 pos | 4 pos | 1.2 ± 0.3 | 129 ± 37 | 477 ± 231 | 5 CAH |
|  |  |  |  |  | 86% | 57% | 86% | 29% | 71% | 57% |  |  |  | 71% |
|  |  |  |  |  | e) | b) | c) | d) | e) | f) | g) | h) | i) | k) |

NON-RESPONDER PATIENTS
Pretreatment anti-PreS1 markers

| Name | Age | Sex | Treatm | Follow-up | IgG anti-preS1 | | | IgM anti-preS1 | | | IgM a-HBc | ALT | HBV-DNA | Hist |
|---|---|---|---|---|---|---|---|---|---|---|---|---|---|---|
|  |  |  |  |  | 21-32 | 32-47 | 94-117 | 21-32 | 32-47 | 94-117 |  |  |  |  |
| Firlag | Po 8 | M | ST/IFN | Fu 6 | pos | pos | neg | neg | neg | neg | 0.3 |  | 210 | CPH |
| alpha-9 | Ch 37 | M | ST/IFN | Fu 6 | neg | neg | neg | neg | neg | neg | 0.8 | 40 | 14,310 | CAH |
| 698 | Po 2 5/6 | M | IFN | Fu 6 | pos | pos | neg | neg | neg | neg | 0.2 | 157 |  | CAH |
| 960 | Po 3 4/12 | F | IFN | Fu 6 | neg | neg | neg | neg | pos | pos | 0.2 | 11 |  | CAH |
| 550 | Po 1 y 8/12 | M | IFN | Fu 6 | neg | neg | neg | neg | neg | neg | 0.3 | 92 |  | CAH |
| 4083 | Po 2 | M | IFN | Fu 6 | neg | pos | neg | pos | pos | pos | 0.3 | 25 |  | CAH |
| 2295 | Po 4 5/12 | M | IFN | Fu 3 | neg | pos | neg | neg | neg | neg | 1.1 |  |  | CAH |
| 4168 | Po 2 | F | IFN | Fu 3 | neg | neg | neg | pos | neg | neg | 0.5 | 83 |  | CPH |
| 3572 | Po 6 y 4 mo | M | IFN | Fu 3 | neg | neg | neg | pos | neg | neg | 0.5 | 192 |  | CAH |
| 535 | Po 8 y 3 mo | F | IFN | Fu 3 | neg | neg | neg | neg | neg | pos | 0.4 | 27 |  | CAH |
| A11 | Ch 39 | M | IFN | Fu 2 | pos | pos | neg | neg | neg | pos | 1.7 | 385 |  | CAH |
| A4 | Ch 38 | M | IFN | Fu 1 | pos | neg | neg | neg | neg | neg | 6.1 | 51 | 157 | CAH |
| B4 | Ch 28 | M | IFN | Fu 1 | pos | pos | neg | neg | neg | neg |  | 40 |  | CAH |
| n = 13 |  |  |  |  | 5 pos | 6 pos | 0 pos | 4 pos | 2 pos | 4 pos | 1.0 ± 0.5 | 100 ± 33 | 4892 ± 4708 | 10 CAH |
|  |  |  |  |  | a) | b) | c) | d) | e) | f) | g) | h) | i) | k) |
|  |  |  |  |  | 38% | 46% | 0% | 31% | 15% | 31% |  |  |  | 77% |
|  |  |  |  |  | NS | NS | p < 0.0005 | NS | NS | NS | NS | NS | NS | NS |

*difficult to judge whether this patient is a R or NR

The invention claimed is:

1. A method of determining whether an individual having chronic hepatitis B virus (HBV) infection will respond to interferon alpha (IFNα) treatment, the method comprising:
   i) obtaining a pre-treatment sample from said chronic HBV-infected individual, and
   ii) analyzing said pre-treatment sample for the presence or absence of IgG antibodies reactive with a preS1 peptide consisting of the sequence of residues 94-117 (SEQ ID NO:1);
   wherein the presence of said IgG antibodies in said pre-treatment sample indicates that said individual will respond to said treatment and the absence of said IgG antibodies in said pre-reatment sample indicates that said individual will not respond to said treatment.

2. The method according to claim 1 wherein the individual is HBeAg positive.

3. The method according to claim 1 wherein the individual is HBeAg negative.

4. The method according to claim 1 wherein the pre-treatment sample is a blood, serum or plasma sample.

5. The method according to claim 1 wherein step (ii) comprises:
   contacting the pre-treatment sample with a preS1 peptide consisting of the sequence of residues 94-117 (SEQ ID NO:1) and;
   detecting the presence or absence of binding of said IgG antibodies to said preS1 peptide.

6. The method according to claim 5 wherein the preS1 peptide comprises a detectable label.

7. The method according to claim 5 wherein said preS1 peptide is immobilised.

8. The method according to claim 5 wherein said binding is detected with a labelled secondary antibody.

9. A method of treating a chronic HBV infection in an individual identified as being responsive to IFNα comprising:
   i) obtaining a pre-treatment sample from a chronic HBV-infected individual, and
   ii) analyzing said pre-treatment sample for the presence or absence of IgG antibodies reactive with a preS1 peptide consisting of the sequence of residues 94-117 (SEQ ID NO:1);
   wherein the presence of said IgG antibodies in said pre-treatment sample indicates that said individual will respond to IFNα treatment, and;
   administering IFNα to said individual identified as being responsive to IFNα.

10. The method according to claim 9 further comprising administering corticosteroid to said individual identified as being responsive to IFNα.

* * * * *